US008557542B2

(12) United States Patent
Suga et al.

(10) Patent No.: US 8,557,542 B2
(45) Date of Patent: Oct. 15, 2013

(54) METHODS FOR RIBOSOMAL SYNTHESIS OF POLYPEPTIDES CONTAINING UNNATURAL N-TERMINAL GROUPS AND APPLICATIONS THEREOF

(75) Inventors: Hiroaki Suga, Tokyo (JP); Hiroshi Murakami, Tokyo (JP); Yuki Goto, Tokyo (JP); Atsushi Ohta, Tokyo (JP)

(73) Assignee: The University of Tokyo, Tokyo (JP)

( * ) Notice: Subject to any disclaimer, the term of this patent is extended or adjusted under 35 U.S.C. 154(b) by 372 days.

(21) Appl. No.: 12/515,074

(22) PCT Filed: Nov. 13, 2007

(86) PCT No.: PCT/JP2007/071986
§ 371 (c)(1),
(2), (4) Date: May 15, 2009

(87) PCT Pub. No.: WO2008/059823
PCT Pub. Date: May 22, 2008

(65) Prior Publication Data
US 2011/0275119 A1    Nov. 10, 2011

(30) Foreign Application Priority Data
Nov. 17, 2006   (JP) ................................. 2006-312000

(51) Int. Cl.
*C12P 21/06*  (2006.01)
(52) U.S. Cl.
USPC ....................................................... 435/69.1
(58) Field of Classification Search
None
See application file for complete search history.

(56) References Cited

U.S. PATENT DOCUMENTS 5,821,052 A * 10/1998 Chen et al. .................... 435/6.11
7,622,248 B2 * 11/2009 Suga et al. .................... 435/6.13
2009/0281280 A1 * 11/2009 Suga et al. .................... 530/333

OTHER PUBLICATIONS

Goto et al., Translation initiation by using varioius N-acylaminoacyl tRNAs; Nucleic Acids Symposium Series, No. 50, pp. 293-294, Nov. 1, 2006.*
Goto et al., Translation initiation by using varioius N-acylaminoacyl tRNAs; Nucleic Acids Symposium Series, No. 50, pp. 293-294, Nov. 2006.*
Murakami et al. A highly flexible tRNA acylation method for nonnatural polypeptide synthesis; Nature Methods, vol. 3, No. 5, pp. 357-360, May 2006.*
Taki et al., Specific N-Terminal Biotinylation of a Protein In Vitro by a Chemically Modified tRNAbet can Support the Native Activity of the Translated Protein; J Biosci Bioeng, vol. 92, No. 2, 149-153, 2001.*
Bessho et al., A tRNA aminoacylation system for non-natural amino acids based on a programmable ribozyme; vol. 20, pp. 723-728, 2002.*
Mamaev et al., Cell-free N-terminal protein labeling using initiator suppressor tRNA; Analytical Biochemistry, vol. 326, pp. 25-32, 2004.*
Taki et al., A novel immobilization method of an active protein via in vitro N-terminal specific incorporation system of nonnatural amino acids; NAR Supplement No. 1, pp. 197-198, 2001.*
Ramesh et al., Expression of *Escherichia coli* Methionyl-tRNA Formyltransferase in *Saccharomyces cerevisiae* Leads to Formylation of the Cytoplasmic Initiator tRNA and Possibly to Initiation of Protein Synthesis with Formylmethionine; MCB, vol. 22, No. 15, pp. 5434-5442, 2002.*
Extended European Search Report dated Feb. 4, 2010 for corresponding European Applicaiton No. 07831716.1.
Goto et al., "Translation initiated by using various N-acylaminoacyl tRNAs," Nucleic Acids Symposium Series No. 50. Nov. 2006. PP. 293-294, XP002564827 ISSN: 1746-8272.
Hendrickson et al., "Incorporation of Nonnatural Amino Acids Into Proteins," Annu. Rev. Biochem., vol. 73, 2004, pp. 146-176.
Kourouklis et al., "Programmable ribozymes for mischarging tRNA with nonnatural amino acids and their applications to translation," Methods, vol. 36. No. 3, Jul. 1, 2005, pp. 239-244, XP004997376 ISSN 1046-2023.
Murakami et al., "A Versatile tRNA Aminoacylation Catalyst Based on RNA," Chemistry & Biology, vol. 10, No. 7, Jul. 1, 2003, pp. 655-662. XP003013894 ISSN: 1074-5521.
Murakami et al., "Flexizymes as a versatile tRNA acylation catalyst and the application for translation," Nucleic Acids Symposium Series No. 50, Nov. 2006, pp. 35-36, XP002564828.
Murakami et al., "Using a Solid-Phase Ribozyme Aminoacylation System to Reprogram the Genetic Code," Chemistry & Biology, vol. 10. Jan. 2003, pp. 1077-1084, XP003013895 ISSN: 1074-5521.
Ohuchi et al., "The flexizyme system: a highly flexible tRNA aminoacylation for the translation apparatus," Current Opinion in Chemical Biology, vol. 11, No. 5, Oct. 1, 2007, pp. 537-542, XP022323966 ISSN: 1367-5931.
Umesh Varshney et al., "Initiation of protein synthesis from a termination codon", Proc. Natl. Acad. Sci., vol. 87, pp. 1586-1590, Feb. 1990, Biochemistry.
Ranjan Chattapadhyay et al., "Initiation of in Vivo Protein Synthesis with Non-Methionine Amino Acids", Biochemistry, American Chemical Society, vol. 29, No. 18, May 8, 1990, pp. 4263-4268.

(Continued)

*Primary Examiner* — Celine Qian
*Assistant Examiner* — Addison D Ault
(74) *Attorney, Agent, or Firm* — Birch, Stewart, Kolasch & Birch, LLP.

(57) ABSTRACT

The present invention aims to synthesize a polypeptide having an unnatural structure at the N-terminus via a biosynthetic process by translation of amino acid sequence information encoded by a nucleic acid. A polypeptide having any amino acid at the N-terminus is synthesized by using an ARS ribozyme that catalyzes the acylation of tRNA with any amino acid to attach any amino acid to an initiator tRNA, thereby initiating a translation with the initiator tRNA.

17 Claims, 24 Drawing Sheets

(56) References Cited

OTHER PUBLICATIONS

Christine Mayer et al., "Anticodon Sequence Mutants of *Escherichia coli* Initiator tRNA: Effects of Overproduction of Aminoacyl-tRNA Synthetases, Methionyl-tRNA Formyltransferase, and Initiation Factor 2 on Activity in Initiation", Biochemistry, American Chemical Society, 2003, 42, pp. 4787-4799.

Sadanand Gite et al., "Ultrasensitive Fluorescence-Based Detection of Nascent Proteins in Gels", Analytical Biochemistry, 279, pp. 218-225, (2000).

Wieslaw Kudlicki et al., "Chaperone-dependent Folding and Activation of Ribosome-bound Nascent Rhodanese", J. Mol. Biol., (1994), 244, pp. 319-331.

Vasanthi Ramachandiran et al., "Fluorophores at the N Terminus of Nascent Chloramphenicol Acetyltransferase Peptides Affect Translation and Movement through the Ribosome", The Journal of Biological Chemistry, vol. 275, No. 3, Jan. 21, 2000, pp. 1781-1786.

Bryan McIntosh et al., "Initiation of protein synthesis with fluorophore-Met-tRNA$_f$ and the involvement of IF-2", Biochimie 82, (2000), pp. 167-174.

Masumi Taki et al., "Specific N-Terminal Biotinylation of a Protein In Vitro by a Chemically Modified tRNA$^{fmet}$ can Support the Native Activity of the Translated Protein", Journal of Bioscience and Bioengineering, vol. 92, No. 2, pp. 149-153, 2001.

Sergey Mamaev et al., "Cell-free N-terminal protein labeling using initiator suppressor tRNA", Analytical Biochemistry, 326, (2004), pp. 25-32.

Jerzy Olejnik et al., "N-terminal labeling of proteins using initiator tRNA", Methods, 36, (2005), pp. 252-260.

Hiroshi Murakami et al., "A highly flexible tRNA acylation method for non-natural polypeptide synthesis", Nature Methods, vol. 3, No. 5, May 2005, pp. 357-359.

C. Mayer et al., "Conformational change of *Escherichia coli* initiator methionyl-tRNAfMet upon binding to methionyl-tRNA formyl transferase" Nucleic Acids Research, 2002, vol. 30, No. 13, pp. 2844-2850.

Office Action dated Jul. 27, 2011 for corresponding European Application No. 0783176.1.

T. Nagase et al., "Differential transcriptional control of the two tRNAfMet genes of *Esherichia coli* K-12" Gene, 1988, vol. 67, pp. 49-57.

T. Ueda et al., "Pure Approach for Cell-Free Translation System", Seibutsubutsuri, 2003, vol. 43., No. 1, pp. 9-14.

Forster et al., "A simplified reconstitution of mRNA-directed peptide synthesis:activity of the epsilon enhancer and an unnatural amino acid", Anal Biachem 297 (1), 60-70, 2001.

Forster et al., "Programming peptidomimetic syntheses by translating genetic codes designed de novo," Proceedings of the National Academy of Sciences of the United States of America, vol. 100, No. 11, pp. 6353-6357, 2003.

Josephson et al., "Ribosomal sunthesis of unnatural peptides," Journal of the American Chemical Society, vol. 127, No. 33, pp. 11727-11735, 2005.

Shimizu et al., "Cell-free translation reconstituted with purified components" Nat Biotechnol 19 (8), 751-755,2001.

\* cited by examiner

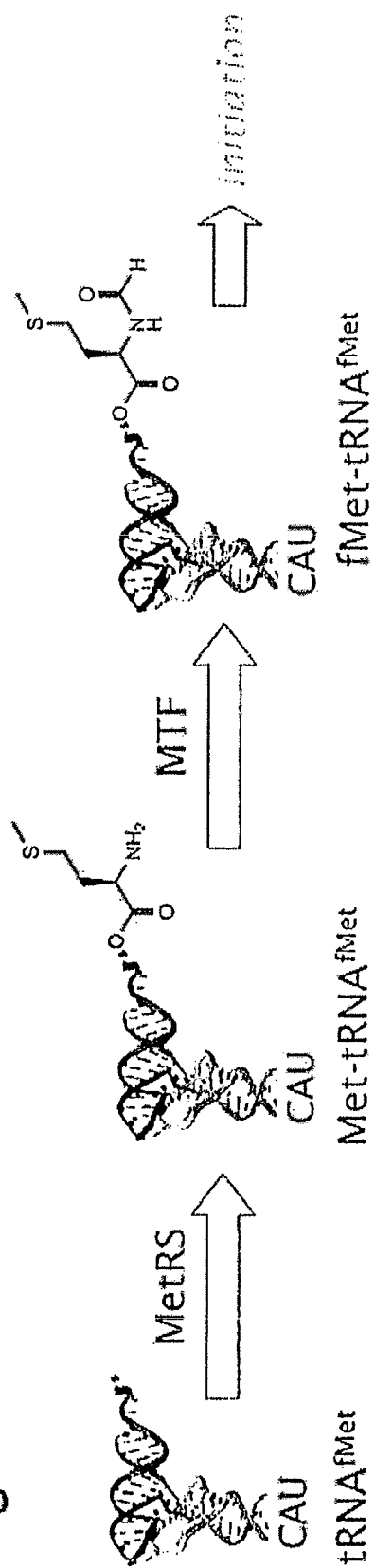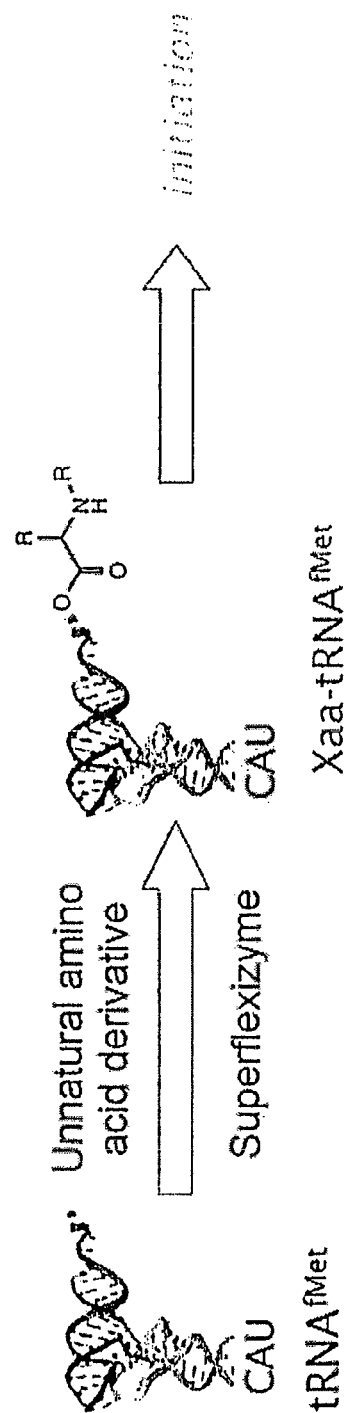
Figure 1A
Figure 1B (A)

(B)

(C) <EDEGSEATGFLPAAGEKTSGPLGNLAEELNGYSRKKGGFSFRF-NH₂
(<E = Pyroglutamic acid)

(A)

5'-GGCGGGGUGGAGCAGCCUGGUAGCUCGUCGGGCUCAUAACCCGAAGAUCGUCGGUUCAAAUCCGGCCCCCGCAACCA-3'

(B)

pyE-Phe-CME

DPhe-Phe-CME

DPhe-CME

Pen-DPhe-CME

HEPES (7.5)
2h

NC　F　CBAF　NC

CBAF 70　54 wt  No aa  CBAF
100  131

CBAF

| wt | Noaa tRNA | (PC) Phe | DF-DF-F |
|---|---|---|---|
| 100 | 0.9 | 76 | 99 |

| Start codon | AUG | | | | AUA | | | | CGG | | | |
|---|---|---|---|---|---|---|---|---|---|---|---|---|
| | -aa | Met | Tyr | Pro | -aa | Met | Tyr | Pro | -aa | Met | Tyr | Pro |

| CCG | | | | GGC | | | | GCC | | | |
|---|---|---|---|---|---|---|---|---|---|---|---|
| -aa | Met | Tyr | Pro | -aa | Met | Tyr | Pro | -aa | Met | Tyr | Pro |

YG1; ATG ACG ACG ACG TTC GGG GGG ACG ACG *flag*
*DF-DF-*F  T    T    T   F   G   G   T   T *FLAG*

SEQUENCE LISTING

```
<160> NUMBER OF SEQ ID NOS: 22

<210> SEQ ID NO 1
<211> LENGTH: 77
<212> TYPE: RNA
<213> ORGANISM: Artificial Sequence
<220> FEATURE:
<223> OTHER INFORMATION: initiator tRNA (tRNA fMet)

<400> SEQUENCE: 1
ggcggggugg agcagccugg uagcucgucg ggcucauaac ccgaagaucg ucgguucaaa    60
uccggccccc gcaacca                                                   77

<210> SEQ ID NO 2
<211> LENGTH: 77
<212> TYPE: RNA
<213> ORGANISM: Artificial Sequence
<220> FEATURE:
<223> OTHER INFORMATION: initiator tRNA with substituted anticodon
<220> FEATURE:
<221> NAME/KEY: misc_feature
<222> LOCATION: (35)..(37)
<223> OTHER INFORMATION: anticodon
<220> FEATURE:
<221> NAME/KEY: misc_feature
<222> LOCATION: (35)..(37)
<223> OTHER INFORMATION: n stands for any base

<400> SEQUENCE: 2
ggcggggugg agcagccugg uagcucgucg ggcunnnaac ccgaagaucg ucgguucaaa    60
uccggccccc gcaacca                                                   77

<210> SEQ ID NO 3
<211> LENGTH: 45
<212> TYPE: RNA
<213> ORGANISM: Artificial Sequence
<220> FEATURE:
<223> OTHER INFORMATION: Super Flexizyme eFx

<400> SEQUENCE: 3
ggaucgaaag auuuccgcgg ccccgaaagg ggauuagcgu uaggu                    45

<210> SEQ ID NO 4
<211> LENGTH: 46
<212> TYPE: RNA
<213> ORGANISM: Artificial Sequence
```

```
<220> FEATURE:
<223> OTHER INFORMATION: Super Flexizyme dFx

<400> SEQUENCE: 4
ggaucgaaag auuccgcau ccccgaaagg guacauggcg uuaggu         46

<210> SEQ ID NO 5
<211> LENGTH: 49
<212> TYPE: DNA
<213> ORGANISM: Artificial Sequence
<220> FEATURE:
<223> OTHER INFORMATION: Synthetic oligonucleotide: P1

<400> SEQUENCE: 5
gtaatacgac tcactatagg cggggtggag cagcctggta gctcgtcgg     49

<210> SEQ ID NO 6
<211> LENGTH: 44
<212> TYPE: DNA
<213> ORGANISM: Artificial Sequence
<220> FEATURE:
<223> OTHER INFORMATION: Synthetic oligonucleotide: P2

<400> SEQUENCE: 6
gaaccgacga tcttcgggtt atgagcccga cgagctacca ggct          44

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide: P3

<400> SEQUENCE: 7
gcatatgtaa tacgactcac tatag                               25

<210> SEQ ID NO 8
<211> LENGTH: 38
<212> TYPE: DNA
<213> ORGANISM: Artificial Sequence
<220> FEATURE:
<223> OTHER INFORMATION: Synthetic oligonucleotide: P4

<400> SEQUENCE: 8
tggttgcggg ggccggattt gaaccgacga tcttcggg                 38

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide: P5

<400> SEQUENCE: 9
tggttgcggg ggccggattt                                     20

<210> SEQ ID NO 10
<211> LENGTH: 27
<212> TYPE: DNA
<213> ORGANISM: Artificial Sequence
<220> FEATURE:
<223> OTHER INFORMATION: Synthetic

<400> SEQUENCE: 10
atgacgacga cgttcggggg gacgacg                             27
```

```
<210> SEQ ID NO 11
<211> LENGTH: 9
<212> TYPE: PRT
<213> ORGANISM: Artificial Sequence
<220> FEATURE:
<223> OTHER INFORMATION: Synthetic

<400> SEQUENCE: 11

Met Thr Thr Thr Phe Gly Gly Thr Thr
1               5

<210> SEQ ID NO 12
<211> LENGTH: 18
<212> TYPE: DNA
<213> ORGANISM: Artificial Sequence
<220> FEATURE:
<223> OTHER INFORMATION: Synthetic

<400> SEQUENCE: 12
atgaagaaga agacgacg                                                 18

<210> SEQ ID NO 13
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid

<400> SEQUENCE: 13

Xaa Lys Lys Lys Thr Thr
1               5

<210> SEQ ID NO 14

<400> SEQUENCE: 14

000

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
atgacgacga cgttcggggg gacgacg                                       27

<210> SEQ ID NO 16

<400> SEQUENCE: 16

000

<210> SEQ ID NO 17
<211> LENGTH: 43
<212> TYPE: PRT
<213> ORGANISM: Artificial Sequence
<220> FEATURE:
<223> OTHER INFORMATION: Neuropeptide: GPCR103 ligand
<220> FEATURE:
<221> NAME/KEY: misc_feature
<222> LOCATION: (1)..(43)
<223> OTHER INFORMATION: Any Xaa is Pyroglutamic acid
```

```
<400> SEQUENCE: 17

Xaa Asp Xaa Gly Ser Xaa Ala Thr Gly Phe Leu Pro Ala Ala Gly Xaa
1               5                   10                  15

Lys Thr Ser Gly Pro Leu Gly Asn Leu Ala Xaa Xaa Leu Asn Gly Tyr
            20                  25                  30

Ser Arg Lys Lys Gly Gly Phe Ser Phe Arg Phe
        35                  40

<210> SEQ ID NO 18
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: "F" N-terminal substrate (F = phenylalanine
      (Phe)) and FLAG tag at C-terminal

<400> SEQUENCE: 18

Phe Thr Thr Thr Phe Gly Gly Thr Thr
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: "Ac" N-terminal substrate (Ac = acetyl) and
      FLAG tag at C-terminal

<400> SEQUENCE: 19

Phe Thr Thr Thr Phe Gly Gly Thr Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: "Pen" N-terminal substrate (Pen = pent-4-enoyl)
      and FLAG tag at C-terminal

<400> SEQUENCE: 20

Phe Thr Thr Thr Phe Gly Gly Thr Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: "Hex" N-terminal substrate (Hex = hexanoyl) and
      FLAG tag at C-terminal

<400> SEQUENCE: 21

Phe Thr Thr Thr Phe Gly Gly Thr Thr
1               5
```

-continued

```
<210> SEQ ID NO 22
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: "Mhe" N-terminal substrate (Mhe = 5-methyl-
      hexanoyl) and FLAG tag at C-terminal

<400> SEQUENCE: 22

Phe Thr Thr Thr Phe Gly Gly Thr Thr
1               5
```

US 8,557,542 B2

METHODS FOR RIBOSOMAL SYNTHESIS OF POLYPEPTIDES CONTAINING UNNATURAL N-TERMINAL GROUPS AND APPLICATIONS THEREOF

TECHNICAL FIELD

The present invention relates to novel processes for synthesizing a polypeptide having a desired N-terminal structure.

BACKGROUND ART (1) Biosynthesis of Polypeptides (Proteins)

In the biosynthesis of polypeptides, the stage during which a polypeptide is produced from a template mRNA is called translation. A set of three consecutive nucleotides in mRNA is called codon. Each codon corresponds to one amino acid, but the three codons UAA, UAG and UGA have no corresponding amino acid and signal a termination of polypeptide synthesis so that they are called stop codons. On the other hand, the first codon AUG in the translation of mRNA, which signals an initiation of polypeptide synthesis, is called start codon. Each set of three nucleotides following the start codon corresponds to one amino acid.

In translation, it is important that a cognate amino acid should be correctly assigned to the tRNA having the function of reading each codon on the mRNA used as a template for polypeptide synthesis. Chemically, translation is achieved via ester linkage of an amino acid to the 3'-end of a specific tRNA at the carboxyl group. For example, methionine binds to an initiator tRNA (or tRNA$^{fMet}$) corresponding to the start codon, then its amino group is formylated (attached to a —COH group) to form N-formylmethionine (FIG. 1A: translation initiation in nature). Thus, the prokaryotic initiator tRNA (fMet-tRNA$^{fMet}$) is synthesized. AUG is the only codon corresponding to methionine.

The AUG codon is also important as a start codon that signals the ribosome to "initiate" protein translation from mRNA. The ribosome is a protein synthesizer consisting of an assembly of 50 or more ribosomal proteins and several RNA molecules (rRNA), which reads genetic information of mRNA to catalyze amino acid polymerization. The ribosome is very similar in structure and function between eukaryotes and prokaryotes, and forms a complex of a molecular mass exceeding several million daltons consisting of one large subunit and one small subunit.

The process of initiating the synthesis of prokaryotic-derived polypeptides involves a number of steps in which proteins called initiation factors (IFs) participate. First, an initiator tRNA aminoacylated with methionine is converted into N-formylmethionine-tRNA by a methionine tRNA formyltransferase (MTF) and binds to an initiation factor. Then, the ribosomal small subunit binds to this initiation factor/N-formylmethionine-tRNA conjugate, and the resulting complex binds to the ribosome-binding site (SD sequence) on mRNA. When this complex finds a start signal (AUG codon), the large subunit binds to it. At the same time, the initiation factor dissociates from the complex, and a ribosome/initiator tRNA complex remains on mRNA. Initiation of translational peptide synthesis occurs through a correct sequence of these steps so that the synthesized product normally has a formylmethionine at the N-terminus.

Then, the ribosome translates codons one after another while moving along mRNA toward the 3'-end, and adds an amino acid to the end to be elongated of the polypeptide by using tRNA. The amino acid added to the end to be elongated of the polypeptide chain is chosen by complementary base pairing between the anticodon of the tRNA molecule to which the amino acid is bound and the subsequent codon of the mRNA strand. In this manner, amino acids corresponding to the codons of mRNA are joined by peptide linkages one after another so that polypeptide synthesis proceeds.

(2) Amino Acid Specificity of tRNA

As already noted, it is tRNA that plays a role as an adapter assigning the codons of mRNA as genetic information to amino acids. Each tRNA acts as an adapter by binding to (aminoacylating) an amino acid specific to it. As a crucial factor for translation accuracy, a strict correspondence is required between the anticodon of each tRNA and an amino acid. However, tRNA and the anticodon do not directly choose an amino acid, but an aminoacyl-tRNA synthetase (ARS) shows specificity to each amino acid, and each tRNA molecule specifically recognizes its cognate ARS and is aminoacylated to accept a correct amino acid. In other words, the amino acid specificity of tRNA in vivo is maintained by specific molecular recognition between tRNA and ARS.

On the other hand, methods for mischarging tRNA with a substance other than the amino acid that should be originally accepted were proposed by artificially changing the specific correspondence among the three members, i.e., tRNA, ARS, and amino acid. One of such methods uses an ARS ribozyme developed by us via in vitro molecular evolution, which catalyzes tRNA acylation reaction (also known as acylase RNA or commonly called "Superflexizyme"). Superflexizyme is characterized in that it allows aminoacylation using any tRNA anti any amino acid. In other words, it allows any tRNA to bind to any amino acid at will. This is very useful for e.g., translationally synthesizing a polypeptide containing an unnatural (unusual) amino acid (patent documents 1, 2, non-patent documents 1, 2, 3, 4).

(3) Cell-free Synthesis

Cell-free polypeptide synthesis is to synthesize a polypeptide in vitro in a genetic information translation system formed of a cytoplasmic extract in an artificial container. Cell-free synthesis using no living organism is free from physiological constraints in vivo, and expected to achieve high-throughput polypeptide synthesis from genes and to dramatically enlarge the range of amino acid sequences that can be synthesized. In principle, it is thought that polypeptides consisting of any amino acid sequence can be synthesized in vitro at will only in the presence of genetic information in cell-free polypeptide synthesis systems unless the catalytic function of the translation enzyme system is disturbed. Moreover, unnatural amino acids not occurring in vivo can also be used if they can be successively assigned to genetic information.

(4) Peptidyl Compounds Having an Unnatural Structure at the N-termini

Naturally derived peptidyl compounds sometimes contain a structurally unique amino acid attached to the N-termini. In the examples shown in FIG. 2, Somamides A [FIG 2A] has a hexyl group and Factor A (A54556 complex) [FIG. 2B] has a 2,4,6-heptatrienyl group exist at the N-termini. Many of neuropeptides found in vivo have a pyroglutamic structure at the N-termini.

These molecules are long peptides that are inevitably expensive because they are difficult to chemically synthesize or they are synthesized at low yields. If one desires to discover a drug by synthesizing a wide variety of mimetic peptides in parallel (library construction), additional molecules encoding the peptide sequences should be chemically conjugated onto beads or peptide molecules, which further adds technical complexity. Moreover, if the peptide library has been exhausted, a completely new library should be synthesized again. On the other hand, no case has been reported in which such a polypeptide was successfuly synthesized through an artificial translation system regardless of whether it is a living cell system or a cell-free system. Thus, if a technique capable of translationally synthesizing these unique peptide molecules by allowing a template mRNA to encode a sequence were developed, a significant technical progress would be made.

References:
  Patent document 1: JPA No. 2003-514572.
  Patent document 2: JPA No. 2005-528090.
  Non-patent document 1: H. Murakami, H. Saito, and H. Suga (2003) "A versatile tRNA aminoacylation catalyst based on RNA" Chemistry & Biology, Vol. 10, 655-662.
  Non-patent document 2: Tanpakushitsu Kakusan Kouso (2003) Vol. 48, No. 11, pp. 1511-1518.
  Non-patent document 3: Jikkenn Igaku (2004) Vol. 22, No. 17, pp. 184-189.
  Non-patent documents 4: H. Murakami, A. Ohta, H. Ashigai, H. Suga (2006) "The flexizyme system: a highly flexible tRNA aminoacylation tool for the synthesis of nonnatural peptides" Nature Methods 3, 357-359.

DISCLOSURE OF THE INVENTION

Problems to be Solved by the Invention

The problem to be solved by the present invention is to synthesize a polypeptide having an unnatural structure (various acyl groups, D-amino acids, other unnatural amino acid structures, etc.) at the N-terminus via a biosynthetic process by ribosomal translation of amino acid sequence information encoded by a nucleic acid.

Means for Solving the Problems

The problem above can be solved by a process of translationally synthesizing a polypeptide having a desired N-terminal structure according to the present invention. Specifically, polypeptides having any amino acid at the N-termini can be synthesized by using an ARS ribozyme that catalyzes the acylation of tRNA with any amino acid to attach any amino acid other than N-formylmethionine to an initiator tRNA, thereby initiating a translation with the initiator tRNA. Amino acids that can be attached to the initiator tRNA include not only natural amino acids commonly used for translation but also amino acids having a desired structure, and even unusual amino acids such as amino acids containing various acyl groups in their amino groups, D-amino acids, beta($\beta$)-amino acids, gamma($\gamma$)-amino acids, delta($\delta$)-amino acids, and N-methylated derivatives of these amino acids, pyroglutamic acids, and aminobenzenecarboxylic acids, and statins ($\beta$-hydroxy-$\gamma$-amino acids, or beta-hydroxy-gamma-amino acids) and derivatives thereof, dipeptides, tripeptides and even longer peptides can be attached to the initiator tRNA. Polypeptides having an unnatural structure at the N-termini can be synthesized via a biosynthetic process by initiating a translation with an amino acid having such an unnatural structure.

Moreover, this synthetic process can be applied to control N-terminal formylation of the translationally synthesized polypeptides by selecting the presence or absence of a methionine tRNA formyltransferase (MTF) in the translation system.

Accordingly, the present application provides the following inventions.

(1) A process for translationally synthesizing a polypeptide having a desired N-terminal structure, comprising the steps of: (a) providing a ribozyme capable of catalyzing the acylation reaction of tRNA; (b) providing an amino acid substrate having a desired structure for use as a substrate for the acylation reaction by the ribozyme; (c) performing an acylation reaction of an initiator tRNA with the amino acid substrate in (b) above using the ribozyme in (a) above to give an initiator tRNA aminoacylated with the amino acid having a desired structure; (d) adding the aminoacylated initiator tRNA obtained in (c) above to a cell-free translation system to initiate a translation with the amino acid having a desired structure, thereby giving a polypeptide having a desired N-terminal structure.

(2) The process of (1) wherein the amino acid that aminoacylates the initiator tRNA in step (c) above is a common amino acid other than methionine.

(3) The process of (1) wherein the amino acid that aminoacylates the initiator tRNA in step (c) above is an unusual amino acid.

(4) The process of (3) wherein the unusual amino acid is selected from the group consisting of amino acids containing various acyl groups in their amino groups, D-amino acids, beta-amino acids, gamma-amino acids, delta-amino acids, and N-methylated derivatives of these amino acids, pyroglutamic acids, statins (beta-hydroxy-gamma-amino acids) and derivatives thereof, dipeptides, tripeptides and longer peptides.

(5) The process of (1) wherein the amino acid substrate provided in step (b) above is a modestly activated amino acid.

(6) The process of (5) wherein the amino acid substrate is a cyanomethyl ester, dinitrobenzyl ester or 4-chlorobenzyl thioester of an amino acid.

(7) The process of any one of (1) to (6) wherein the ribozyme capable of catalyzing the acylation reaction of tRNA is a ribozyme consisting of the RNA sequence (1) or (2) below:

(1)
(SEQ ID NO: 3)
GGAUCGAAAGAUUUCCGCGGCCCCGAAAGGGGAUUAGCGUUAGGU (2)
(SEQ ID NO: 4)
GGAUCGAAAGAUUUCCGCAUCCCCGAAAGGGUACAUGGCGUUAGGU.

8) The process of any one of (1) to (7) wherein the initiator tRNA has a structure consisting of the RNA sequence in the 5'-3' direction shown by:

(SEQ ID NO: 2)
GGCGGGUGGAGCAGCCUGGUAGCUCGUCGGGCUNNNAACCCGAAGAUCG
UCGGUUCAAAUCCGGCCCCCGCAACCA where NNN represents an anticodon consisting of a random nucleotide set, and a start codon corresponding to the anticodon exists on the mRNA encoding the sequence of the polypeptide to be translationally synthesized, and the start codon encodes the amino acid having a desired structure.

(9) The process of (8) wherein the anticodon in the initiator tRNA is CAU and the start codon on the mRNA is AUG.

(10) The process of (8) wherein the anticodon in the initiator tRNA is an anticodon other than CAU and the start codon on the mRNA is a codon other than AUG.

(11) The process of (1), which uses a reconstructed cell-free translation system as the cell-free translation system.

(12) The process of (11) wherein only a polypeptide having a desired N-terminal structure is translationally synthesized by eliminating methionine or a methionyl-tRNA synthetase (MetRS) from the translation system to inhibit the native translation initiation machinery.

(13) The process of (11) wherein the N-terminal formylation of the polypeptide to be translationally synthesized is controlled by selecting the presence or absence of a methionine tRNA formyltransferase (MTF).

(14) A kit usable for translationally synthesizing a polypeptide having an unnatural structure at the N-terminus, comprising the following components:

(a) two ribozymes that catalyze tRNA acylation consisting of the RNA sequence (1) or (2) below:

(1)
(SEQ ID NO: 3)
GGAUCGAAAGAUUUCCGCGGCCCCGAAAGGGGAUUAGCGUUAGGU (2)
(SEQ ID NO: 4)
GGAUCGAAAGAUUUCCGCAUCCCCGAAAGGGUACAUGGCGUUAGGU;

(b) an amino acid substrate having an unnatural structure, for use as a substrate for the ribozymes; (c) an initiator tRNA; and (d) a cell-free synthesis system.

Advantages of the Invention

According to the present invention, polypeptides having a desired structure at the N-termini can be translationally synthesized by preparing an initiator tRNA aminoacylated with an amino acid having a desired structure by an ARS ribozyme capable of attaching tRNA to any amino acid at will and using it to initiate a translation, and even unusual amino acid not occurring in vivo can also be used. Moreover, the N-terminal modification of the polypeptides to be translationally synthesized can be controlled by regulating the translation system.

Thus, the present invention can be applied to N-terminally modified polypeptides in general so that unique long peptide molecules that have been hitherto very difficult to chemically synthesize can be conveniently and inexpensively synthesized.

BRIEF DESCRIPTION OF THE DRAWINGS

FIG. 1 shows a comparison between the initiator tRNA in the native (prokaryotic) translation system and an initiator tRNA in the present invention. FIG. 1A shows translation initiation in nature, and FIG. 1B shows translation initiation in the present invention.

FIG. 2A shows Somamides A, FIG. 2B shows Factor A (A54556 complex), and FIG. 2C shows an example of a neuropeptide (GPCR103 ligand)(SEQ ID NO: 17).

FIG. 4A shows the sequence of a tRNA used for translation initiation (T7 transcript), and FIG. 2B shows its secondary structure. A typical initiator tRNA having an anticodon (CAU) complementary to the common start codon (AUG) is shown.

FIG. 5A shows translation initiation in nature, and FIG. 5B shows translation initiation (with an aminoacylated tRNA) in the present invention.

FIG. 12A shows the sequence (SEQ ID NO: 10 (DNA) and SEQ ID NO: 11 (peptide), FIG. 12B shows the results of translational synthesis, FIG. 12C shows reaction conditions, and FIG. 12D explains the chemical structures represented by abbreviations such as Ac, Pen, Hex, Mhe.

THE MOST PREFERRED EMBODIMENTS OF THE INVENTION (1) Amino Acids

Amino acids basically refer to compounds having both amino (—NR$_2$) and carboxyl (—COOH) functional groups in their molecules. Among those, amino acids used for normal translation are the following twenty natural amino acids: alanine (Ala), valine (Val), leucine (Leu), isoleucine (Ile), proline (Pro), tryptophan (Trp), phenylalanine (Phe), methionine (Met), glycine (Gly), serine (Ser), threonine (Thr), tyrosine (Tyr), cysteine (Cys), glutamine (Gln), asparagine (Asn), lysine (Lys), arginine (Arg), histidine (His), aspartate (Asp), and glutamate (Glu), which are alpha-aminocarboxylic acids (or substituted alpha-aminocarboxylic acids) represented by the general structure:

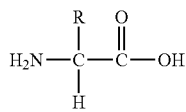

[Formula 1]

wherein R is an amino acid side chain. As used herein, amino acids include both natural and unnatural amino acids, and these natural amino acids are sometimes specifically called common amino acids.

Figure 2:
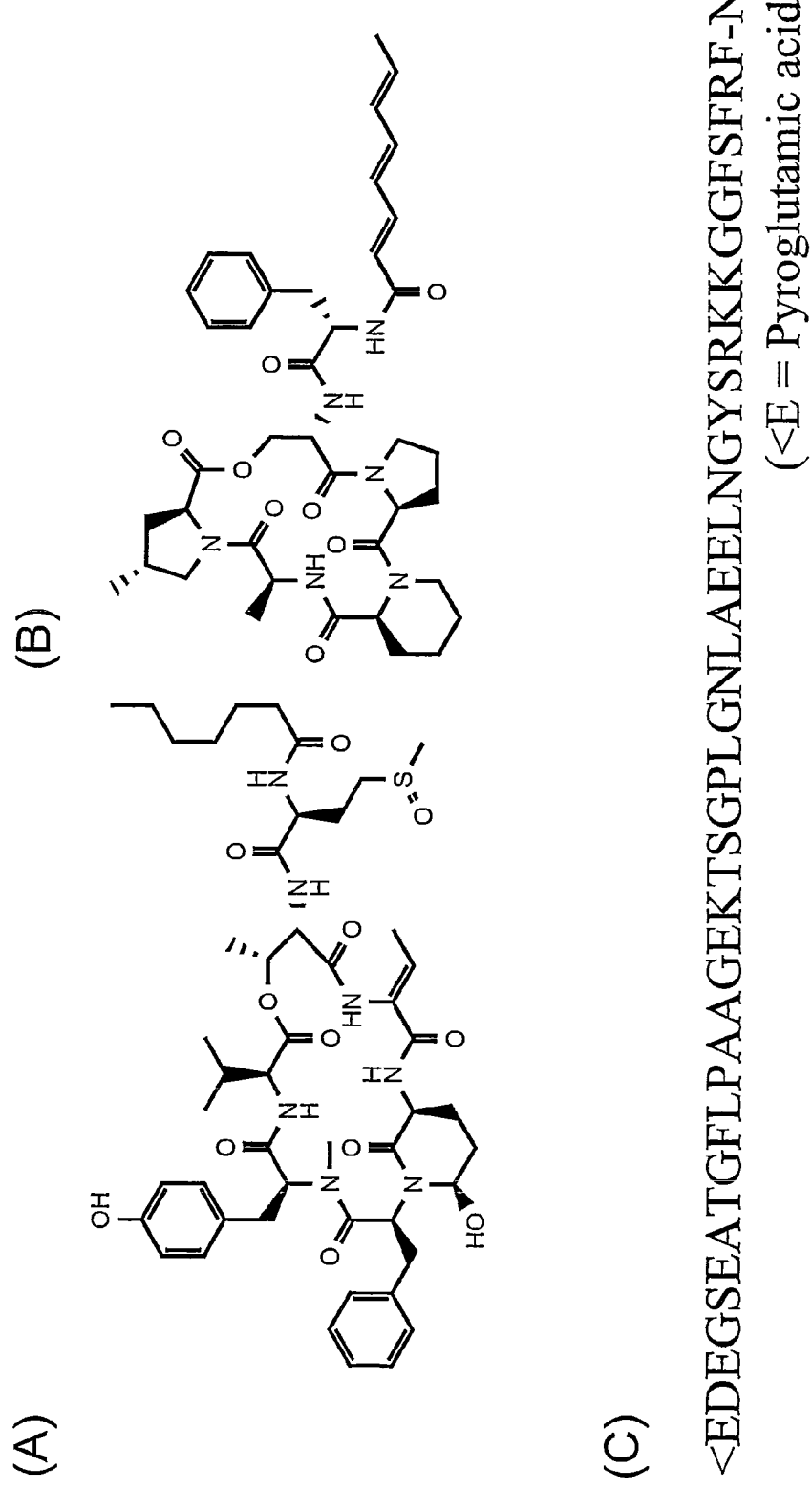
FIG. 2 shows examples of unique structures found in the N-terminal regions of natural peptidyl products.
Figure 3:
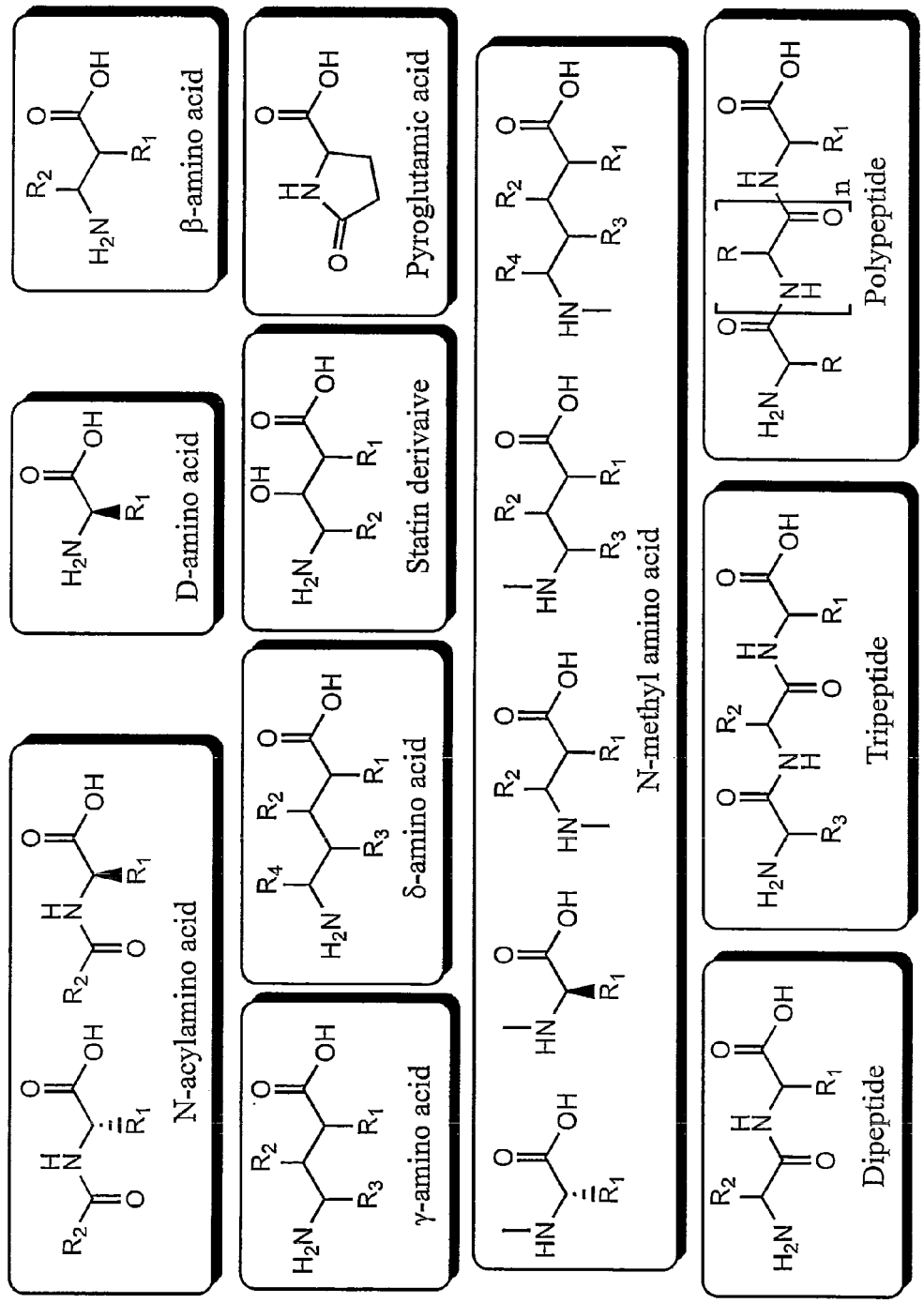
FIG. 3 shows examples of various initiator amino acids used in the present invention.

In contrast to the common amino acid, unusual amino acids refer to amino acids other than the common amino acids, and they may be artificially synthesized or found in nature. Examples of unusual amino acids include beta-amino acids, gamma-amino acids and delta-amino acids containing an additional methylene group in their amino acid structure, and stereoisomers of the common amino acids such as D-amino acids, etc. As used herein, the term amino acid also includes derivatives having a structure in which an amino group or carboxyl group on the amino acid structure has been substituted, and examples of unusual amino acids further include amino acids containing various acyl groups in their amino groups, N-methylated derivatives, statins (beta-hydroxy-gamma-amino acids), pyroglutamic acids, aminobenzenecarboxylic acids, etc. In addition, dipeptides, tripeptides or longer peptides are sometimes also expressed as amino acids. Thus, the reference to "amino acid having a desired structure" includes all of such "amino acids" as used herein. The chemical formulae of representative examples of the various amino acids described above are shown in FIG. 3.

A peptide containing an unusual amino acid is called "unique peptide". Examples of naturally isolated unique peptides include hormone peptides, neuropeptides, Somamides A, factor A, GPCR103 ligand, etc. Unique peptides that can be synthesized by the present invention are not limited to mimetics of these natural unique peptides, but any unique peptide having the various unusual amino acids described above at the N-terminus can be synthesized.

(2) Initiator tRNA

The initiation of translation of mRNA requires a specific tRNA called initiator tRNA. Translation begins when an aminoacylated initiator tRNA binds to the ribosomal small subunit together with an initiation factor (IF) and the ribosomal small subunit binds to a start codon on mRNA, and the start codon is recognized by the initiator tRNA. As described in the section of Background Art, the initiator tRNA always carries methionine (formylmethionine in the case of prokaryotic cells) and the methionine codon AUG is normally used as the start codon in nature so that the initiator tRNA has an anticodon corresponding to methionine.

In contrast, the present invention is characterized in that the initiator amino acid is not limited to methionine. In other words, it is characterized in that translation is initiated by attaching any amino acid other than methionine to the initiator tRNA. In the present invention, the start codon is not limited to AUG, either. Thus, other codons can also be assigned as start codons. In the present invention, therefore, the initiator tRNA may have an anticodon corresponding to methionine or may be substituted by another anticodon. For example, we found that translation can be initiated with even AUA, CGG, CCG, GGC and GCC codons so far as initiator tRNAs having their anticodons are used.

The nucleotide sequence of the native initiator tRNA (tRNA$^{fMet}$) corresponding to the start codon AUG that can be used in the present invention is shown below.

Figure 4:
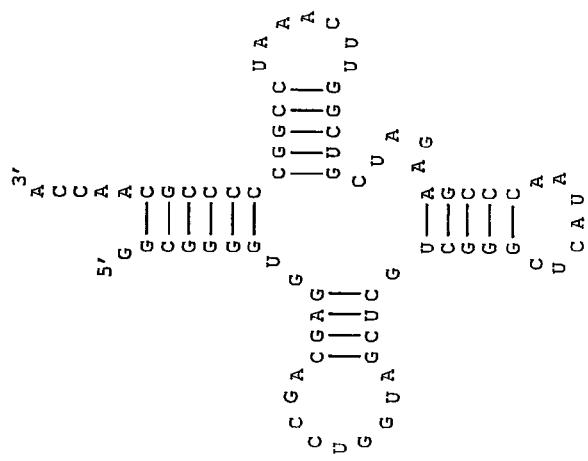
FIG. 4 (SEQ ID NO: 1) shows examples of initiator tRNAs that can be used in the present invention.

5'-GGCGGGGUGGAGCAGCCUGGUAGCUCGUCG-GGCUCAUAACCCGAAGAUCGUCGGUUCAAAUCC-GGCCCCCGCAACCA-3' (SEQ ID NO: 1), where the underlined motif represents an anticodon region. See FIG. 4B showing the secondary structure.

When the start codon is changed, a tRNA having an anticodon complementary to it is used. When a random codon (NNN) is assigned as a start codon, therefore, the sequence of the initiator tRNA is represented as follows.

5'-GGCGGGGUGGAGCAGCCUGGUAGCUCGUCG-GGCUNNNAACCCGAAGAUCGUCGGUUCAAAUCC-GGCCCCCGCAACCA-3' (SEQ ID NO: 2), where the underlined motif NNN represents an anticodon consisting of a random nucleotide set. The sequence except for NNN is the body sequence of tRNA$^{fMet}$, which is thought to be necessary for attaching the initiation factor (IF).

When a polypeptide having a desired N-terminal structure is translationally synthesized, a start codon corresponding to the anticodon represented by NNN above is present on the mRNA encoding the sequence of the polypeptide to be translationally synthesized and the start codon encodes a desired initiator amino acid to be placed at the N-terminus of the polypeptide.

(3) Aminoacylation of Initiator tRNA

Aminoacylation of tRNA is a reaction by which the carboxyl group of an amino acid forms an ester bond with the hydroxyl group at the 3'-end of tRNA (acylation). The amino acid binds to tRNA via an activated intermediate.

In nature, aminoacyl-tRNA is synthesized by ARS protein enzymes that catalyze a two-step reaction involving activation of an amino acid substrate copuled to ATP hydrolysis (a reaction by which a high-energy intermediate aminoacyl-AMP is synthesized from ATP and an amino acid), followed by binding of the amino acid substrate to tRNA. First, the carboxyl group of an amino acid is activated by binding the AMP moiety to form an adenylated amino acid (aminoacyl-AMP). Then, AMP detaches from the adenylated amino acid, and the carboxyl group of the amino acid is transferred to the hydroxyl group of the 3'-terminal ribose of the tRNA. By this transfer, the amino acid forms an activated ester bond with the tRNA, giving an aminoacylated tRNA. The ester bond between the activated amino acid and the tRNA is a high-energy bond that generates a high free energy by hydrolysis, and the energy of this bond is used to elongate the polypeptide chain via covalent linkage of amino acids during the subsequent protein synthesis steps.

In nature, such tRNA aminoacylation reaction is catalyzed by an aminoacyl-tRNA synthetase (ARS) specific to each amino acid and tRNA. The reaction by which methionine is attached to the initiator tRNA is mediated by a dedicated protein enzyme methionyl-tRNA synthetase (MetRS).

In the present invention, however, the aminoacylation of the initiator tRNA takes place by using an ARS ribozyme that is an RNA molecule capable of catalyzing tRNA acylation reaction. ARS ribozymes that can be used in the present invention are ribozymes having the function of acylating any tRNA with an amino acid substrate having a desired structure. Unlike native ARS protein enzymes, such ARS ribozymes do not have specificity to each amino acid and each tRNA and allow aminoacylation with any amino acid other than the amino acid to be charged so that any amino acid can be attached to the initiator tRNA.

Referring to FIG. 1, aminoacylation of initiator tRNA is explained. As also explained in the section of Background Art, fMet-tRNA$^{fMet}$ synthesized from tRNA$^{fMet}$ by two protein enzymes MetRS (methionyl-tRNA synthetase) and MTF (methionine tRNA formyltransferase) acts as an initiator tRNA in nature (FIG. 1A), in contrast to which Xaa-tRNA$^{fMet}$ consisting of tRNA$^{fMet}$ charged with various amino acid derivatives by an ARS ribozyme (Superflexizyme) instead of MetRS acts as an initiator tRNA in the present invention (FIG. 1B).

The ARS ribozymes used in the present invention can be created by the in vitro molecular evolution described by us (Japanese Patent Application No. 2005-352243 entitled "Versatile acylation catalysts and uses thereof", and H. Murakami, A. Ohta, H. Ashigai, H. Suga (2006) "The flexizyme system: a highly flexible tRNA aminoacylation tool for the synthesis of nonnatural peptides" Nature Methods 3, 357-359). Unlike native ARS protein enzymes, the ARS ribozymes created by this method have been evolved to skip the first step of producing a high-energy intermediate (aminoacyl-AMP) in aminoacylation reaction and to catalyze only the step of attaching an amino acid substrate to tRNA, which requires that a preliminarily modestly activated amino acid should be used as an amino acid substrate. In other words, amino acid adenylation is skipped by using an amino acid derivative having a modestly activated ester bond at the carbonyl group where acylation proceeds. Generally, activation of acyl groups can be achieved by linking an electron-withdrawing leaving group via ester bonds, but esters having an extremely strong electron-withdrawing leaving group cause not only hydrolysis in water but also random RNA acylation. Thus, modestly activated amino acid substrates should be used to avoid such side reactions under catalyst-free conditions. Such modest activation can be accomplished by using e.g., AMP, a cyanomethyl ester, a thioester, or a benzyl ester having an electron-withdrawing functional group such as a nitro group or fluorine, etc. Examples of preferred amino acid substrates include an aminoacyl-cyanomethyl ester (CME: cyanomethyl ester), an aminoacyl-dinitrobenzyl ester (DNB: 3,5-dinitrobenzyl ester), or an aminoacyl-4-chlorobenzyl thioester (CBT: p-chloro-benzyl thioester), etc., but the present invention is not limited to these examples and those skilled in the art can screen suitable leaving groups having a high reaction efficiency to use them, and the acylation reaction using an amino acid substrate having such a suitable leaving group is also naturally included in the scope of the present invention.

Very specific examples of ARS ribozymes that can be used in the present invention include Superflexizymes described above in the section of Background Art, i.e., ribozymes consisting of the RNA sequence:

(1)
                            (Superflexizyme eFx: SEQ ID NO: 3)
GGAUCGAAAGAUUUCCGCGGCCCCGAAAGGGGAUUAGCGUUAGGU
or (2)
                            (Superflexizyme dFx: SEQ ID NO: 4)
GGAUCGAAAGAUUUCCGCAUCCCCGAAAGGGUACAUGGCGUUAGGU or a variant thereof. The creation of these Superflexizymes and their precursor Flexizyme are described in detail in Japanese Patent Application No. 2005-352243 entitled "Versatile acylation catalysts and uses thereof"; and H. Murakami, A. Ohta, H. Ashigai, H. Suga (2006) "The flexizyme system: a highly flexible tRNA aminoacylation tool for the synthesis of nonnatural peptides" Nature Methods 3, 357-359; and H. Murakami H. Saito, H. Suga (2003) "A versatile tRNA aminoacylation catalyst based on RNA" Chem. Biol. 10, 655-662.

When these Superflexizymes or variants thereof are used as ARS ribozymes, their amino acid substrates must have an aromatic ring in their amino acid side chain or leaving group so that they can be recognized by the Superflexizymes. The structure of such amino acid substrates is represented by the general formula below.

[Formula 2]

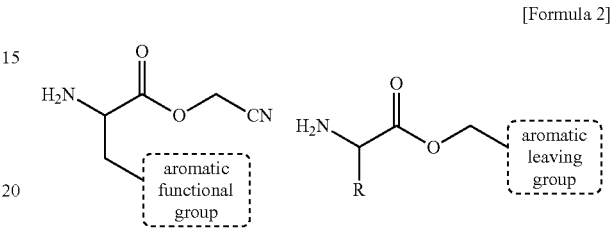

As for the synthesis of cyanomethyl esters of amino acids having an aromatic ring as a side chain (structural formula at left) among amino acid substrates, see the methods described in JPA No. 2005-528090 and Suga et al., J. Am. Chem. Soc., 120, 1151 to 1156, 1998. The examples herein below show synthetic examples of N-acylated amino acid substrates and peptide substrates containing a cyanomethyl ester (CME).

Synthesis of an amino acid substrate having an aromatic ring as a leaving group (structural formula at right) begins with (1) reacting an amino acid having a Boc-protected amine with a compound having a halogen at the benzyl position and an electron-withdrawing group in the aromatic moiety to form an ester. Then, the Boc protecting group is removed by using an acid to synthesize an amino acid substrate. Alternatively, this ester can also be synthesized by (2) condensing an amino acid having a Boc-protected amine with a compound having a hydroxyl group at the benzyl position and an electron-withdrawing group in the aromatic moiety using a conventional condensing agent. It can also be synthesized by (3) mixing an activated Boc-protected amino acid with a compound having a hydroxyl group at the benzyl position and an electron-withdrawing group in the aromatic moiety. Thioesters can be synthesized by the method (2) or (3) above except that a compound having a thiol group at the benzyl position is used in place of a compound having a hydroxyl group at the benzyl position and an electron-withdrawing group in the aromatic moiety. Thioesters have a relatively high activity so that an electron-withdrawing group is not necessarily required in the aromatic moiety. A specific procedure for synthesizing an amino acid substrate having an aromatic ring as a leaving group has also already been described in Japanese Patent Application No. 2005-352243. The examples herein below show synthetic examples of substrates containing unusual amino acids such as D-amino acids, N-methylated amino acids or β-amino acids incorporating a dinitrobenzyl ester (DBE).

The ARS ribozyme-mediated acylation reaction may be performed in solution or on a column using an ARS ribozyme immobilized on a carrier. When the translation reaction is at a low-volume scale of 100 microliter or less for example, the ARS ribozyme-mediated tRNA acylation may take place in solution and the pellet precipitated with ethanol from the reaction solution may be dissolved in a suitable buffer (e.g., 1 mM potassium acetate, pH 5, etc.) and added to a translation system. Suitable reaction conditions may be chosen as appropriate, but an example of reaction conditions at low-volume scale may involve reacting 0.1 M Reaction Buffer, pH 7.5 containing (final concentrations) 0.5-20 µM tRNA, 0.5-20 µM ARS ribozyme, 2-10 mM amino acid substrate, 0.6 M MgCl$_2$ at 0° C. for 1 hour to 24 hours.

When the translation reaction scale exceeds 100 microliter, it is more convenient to use an ARS ribozyme immobilized on a carrier so that the ARS ribozyme may be recycled. Carriers that can be used include, but not limited to, e.g., resins, agarose, Sepharose, magnetic beads, etc. The reaction using an ARS ribozyme immobilized on a carrier can be performed according to the method, e.g., described in Murakami, H., Bonzagni, N. J. and Suga, H. (2002). "Aminoacyl-tRNA synthesis by a resin-immobilized ribozyme." J. Am. Chem. Soc. 124(24): 6834-6835. The aminoacylated tRNA as the reaction product can be isolated by various methods. As an example, it can be eluted from the column with a buffer containing about 10 mM EDTA. The resin to which the ARS ribozyme is immobilized can be recycled over ten times by equilibration with Reaction Buffer, for example.

As for further details about the ARS ribozyme-mediated acylation reaction, also see the examples herein below. It should be noted that the examples herein below show experimental results using a short analog of the initiator tRNA rather than the initiator tRNA itself in order to conveniently detect acylation with various amino acids. It was found that aminoacylation can be performed with even unusual amino acids such as dipeptides or tripeptides, or longer peptides, amino acids having an unnatural structure at the N-termini (D-amino acids, N-methylated products, beta-amino acids, statins, etc.).

(4) Translation

Polypeptides having any amino acid at the N-termini can be synthesized by adding an initiator tRNA aminoacylated by an ARS ribozyme to a cell-free translation system according to the method described above.

Figure 5:
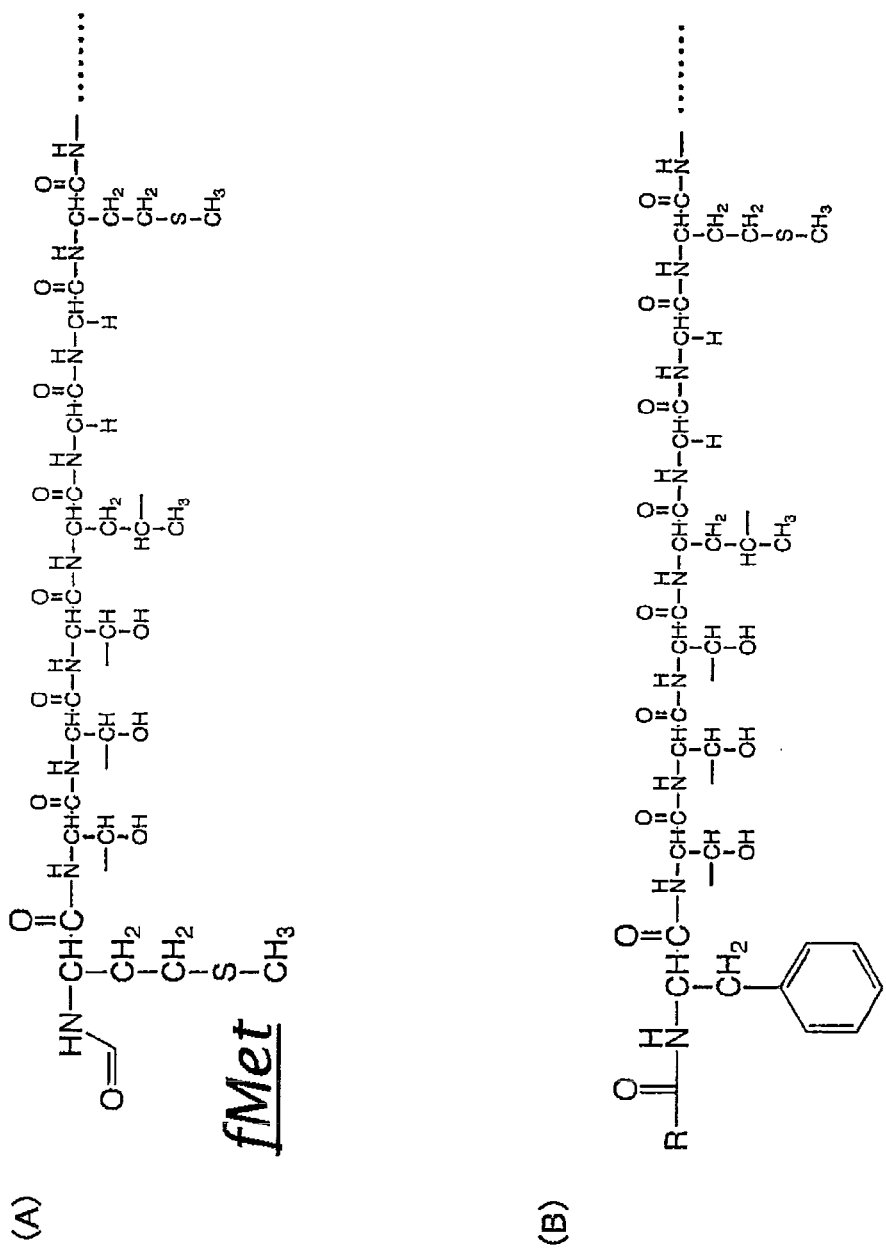
FIG. 5 shows a comparison between the native (prokaryotic) translation product and a translation product in the present invention.

Native translation products exclusively have methionine (formylmethionine in the case of prokaryotic cells) at the N-termini of the polypeptides, but unique peptides having amino acids other than methionine, various acyl groups, D-amino acids, N-methyl amino acids, beta-amino acids, statins and other unique structures at the N-termini can be synthesized at will according to the present invention. FIG. 5 shows the native translation product (FIG. 5A) and an example of a polypeptide that can be synthesized by the present invention (FIG. 5B) (in this example, a phenylalanine derivative having various acyl groups is present at the N-terminus).

In cell-free synthesis systems free from constraints in vivo, polypeptides consisting of any amino acid sequence can be synthesized at will and at any length in principle and even unusual amino acids can be used so far as they could be assigned to genetic information. Thus, polypeptides having a desired N-terminal structure can be synthesized by adding an initiator tRNA aminoacylated with the an amino acid having the desired structure to the system to initiate a translation, and all of the twenty natural amino acids can be used as amino acids introduced during elongation reaction. The natural amino acids for elongation can also be added as aminoacylated tRNA acylated by an ARS ribozyme to a cell-free translation system.

Cell-free translation systems typically comprise a ribosomal protein, an aminoacyl-tRNA synthetase (ARS), a ribosomal RNA, an amino acid, tRNA, GTP, ATP, a translation initiation factor (IF), an elongation factor (EF), a termination factor (RF), and a ribosome recycling factor (RRF), and other factors necessary for translation, and include high-efficiency systems using E. coli extracts or wheat germ extracts. Other systems use rabbit erythrocyte extracts or insect cell extracts. These systems produce several hundred micrograms to several milligrams of proteins/mL by continuous supplying energy under dialysis. Some systems contain an RNA polymerase for simultaneous transcription from a gene's DNA. In the present invention, such cell-free translation systems can be used as appropriate. Commercially available cell-free translation systems that can be used include E. coli-derived systems such as RTS-100® from Roche Diagnostics and PURESYSTEM® from PGI and systems based on wheat germ extracts available from ZOEGENE Corporation and CellFree Sciences Co., Ltd.

Moreover, the systems can be subdivided and their components are reassembled to construct translation systems containing lower levels of impurities. Specific components include ribosomes, GTP, ATP, IF, EF, RF, RRF, a minimum set of tRNA/ARS/amino acid for synthesizing a target peptide, etc. Such reconstructed cell-free translation systems are especially preferred in the present invention because they allow components to be controlled at will, whereby the type of the initiator amino acid or peptide may be freely selected and allow the N-terminal modification of polypeptides to be controlled more flexibly.

For example, the native translation initiation machinery can be inhibited by eliminating methionine or a methionyl-tRNA synthetase (MetRS) from the translation system. Then, an initiator tRNA acylated with an amino acid having a desired structure is added to produce only a peptide having the desired N-terminal structure in the translation system. The initiator tRNA used here is an initiator tRNA$^{fMet}$ having a modified anticodon region. The start codon used in the present invention is not limited to the native AUG codon, but other codons can also be used as start codons, i.e., a specific codon can be assigned to the N-terminal amino acid. In the nucleic acid sequence encoding the translationally synthesized polypeptide here, the start codon on mRNA may be essentially any codon complementary to the anticodon of acyl-tRNA$^{fMet}$ (though the efficiency varies more or less). When prokaryotic-derived systems are used, the template mRNA should contain an SD sequence as a ribosome-binding site near the 5'-end and a start codon downstream of it.

Moreover, N-terminal modification can also be controlled by selecting the presence or absence of a methionine tRNA formyltransferase (MTF) if a reconstructed cell-free translation system is used. MTF is an enzyme capable of attaching a formyl group to the amino group of methionine acylated with the initiator tRNA in prokaryotic-derived systems. Although this enzyme is generally thought to have formylation selectivity for methionine, some previous reports have showed from indirect experimental results that amino groups such as phenylalanine or glutamine attached to the initiator tRNA were modified with a formyl group (Mayer, C., Köhrer, C., Prusko, C., RajBhandary, U. L. (2003). "Anticodon Sequence Mutants of Escherichia coli Initiator tRNA: Effects of Overproduction of Aminoacyl-tRNA Synthetases, Methionyl-tRNA Formyltransferase, and Initiation Factor 2 on Activity in Initiation" Biochemistry 42: 4787-4799). According to the present invention, direct supportive experimental results were obtained by mass spectrometry of synthetic peptides. According to the present invention, it was found that N-terminally formylated polypeptides can also be synthesized by using various additional amino acids.

On the other hand, we also found that N-terminally unformylated polypeptides can be synthesized by eliminating MTF from the translation system and that N-terminally unformylated peptides can also be synthesized whether or not MTF or its donor substrate exists in the system. For translation initiation involving prokaryotic-derived initiation factors, modification with a formyl group or similar acyl group (acetyl group, etc.) has been previously thought mandatory, but the present invention showed that this limitation is removed (by initiating a translation with an initiator tRNA charged with various amino acids by an ARS ribozyme). For example, not only translation can be initiated with an amino acid having no acyl group, but also any R can be attached to the acyl group introduced into the amino group (R-CO-aa-). Moreover, R can be a dipeptide, tripeptide or a longer peptide, or a statin structure, or the amino acid may be a D-amino acid, and formylation does not proceed in peptides when translation is initiated with them, whereby unformylated peptides are synthesized.

In the present invention, therefore, the N-terminal modification of translationally synthesized peptides can be controlled by selecting the type of the initiator amino acid or peptide or the presence or absence of MTF. On the other hand, it was also found that formylation does not proceed at all even in the presence of MTF in the translation system when stereoisomers of common amino acids such as D-amino acids or dipeptides or tripeptide attached to the initiator tRNA were used for translation.

(5) Kits

Kits that can be used to translationally synthesize a polypeptide having an unnatural structure at the N-terminus using the processes described above are also included in the scope of the present invention. The kits may comprise at least:

(a) two ribozymes that catalyze tRNA acylation, consisting of the RNA sequence (1) or (2) below:

(1)
(SEQ ID NO: 3)
GGAUCGAAAGAUUUCCGCGGCCCCGAAAGGGGAUUAGCGUUAGGU (2)
(SEQ ID NO: 4)
GGAUCGAAAGAUUUCCGCAUCCCCGAAAGGGUACAUGGCGUUAGGU each of which may be immobilized on a carrier;

(b) an amino acid substrate having an unnatural structure, for use as a substrate for the ribozymes;

(c) an initiator tRNA; and (d) a cell-free synthesis system; and may further comprise a reaction buffer, a reaction vessel, instructional materials, etc.

Unless otherwise specified, materials and procedures for carrying out the present invention are described in various general textbooks or specialized references and used according to conventional methods well known in the technical fields of chemistry and molecular biology. As for references about molecular biology, see e.g., Sambrook et al., Molecular Cloning: A Laboratory Manual, Second Edition, Cold Spring Harbor Laboratory Press, Cold Spring Harbor, N.Y. (1989); and Ausubel et al., Current Protocols In Molecular Biology, Greene Publishing Associates (1992); and Harlow and Lane, Using Antibodies: A Laboratory Manual, Cold Spring Harbor Laboratory Press, Cold Spring Harbor, N.Y. (1999), etc.

The following examples further explain in detail the invention described above, but they are given for illustrative purposes only and should not be construed to limit the scope of the present invention. Various changes or modifications can be made by those skilled in the art in the light of the description herein and the appended claims, and these changes or modifications are also included in the present invention.

EXAMPLES

In the examples described below, Superflexizymes were used as ARS ribozymes, and a prokaryotic-derived reconstructed cell-free synthesis system additionally comprising a transcription system from cDNA was used as a translation system.

1. Synthesis of Amino Acid Substrates

The present example describes the synthesis of amino acid substrates having modestly activated ester bonds for use as substrates for Superflexizyme-mediated acylation reaction (hereinafter sometimes simply referred to as "substrates"). The substrates had to contain an aromatic ring in their molecules in order that they could be recognized by Superflexizymes. When an aromatic ring was used as a leaving group, the ester bonds were activated by a thioester (CBT), or activated by an ester having an electron-withdrawing functional group in the aromatic moiety (DBE). Amino acids or peptides having an aromatic ring in their side chain were activated by a cyanomethyl ester (CME).

1.1. D-amino Acids, N-methylated Amino Acids, Beta-amino Acids

A typical procedure for synthesizing substrates consisting of the title amino acids containing DBE is explained for D-serine DBE as an example. To 0.4 ml of dimethylformamide were added alpha-N-Boc-D-serine (384 mg, 1.87 mmol), triethylamine (207 mg, 2.05 mmol) and 3,5-dinitrobenzyl chloride (324 mg, 1.50 mmol) and mixed, and the mixture was stirred at room temperature for 12 hours. After the reaction was completed, diethyl ether (15 ml) was added, and the solution was washed with 0.5 M HCl (5 mL×3), 4% $NaHCO_3$ (5 mL×3) and brine (5 mL×1) and dried over magnesium sulfate to remove water in the organic layers, and then the solvent was distilled off under reduced pressure. The crude residue was dissolved in 4M hydrochloric acid/ethyl acetate (3 ml), and the solution was allowed to stand at room temperature for 20 minutes. After the reaction was completed, diethyl ether (3 mL) was added and the solvent was distilled off under reduced pressure three times to remove excessive HCl. Diethyl ether (3 ml) was added to form a precipitate, which was recovered by filtration to give a product at a total yield of 35% (170 mg, 0.53 mmol). $^1H$ NMR (DMSO-d6, 500 MHz) δ 8.83 (s, 1H), 8.70 (s, 2H), 8.44 (br, 3H), 5.56 (s, 2H), 4.07 (d, J=4.6 Hz, 1H), 2.22 (m, 1H), 1.00 (d, J=7.0 Hz, 3H), 0.97 (d, J=6.9 Hz, 3H).

1.2. N-acylated Amino Acids

A typical procedure for synthesizing N-acylated amino acid substrates containing CME (N-acyl-aminoacyl-CME) is explained for N-acetyl-Phe-CME as an example. Phenylalanine (33 mg, 0.20 mmol), N-hydroxysuccinimide acetate (38 mg, 0.24 mmol) and $NaHCO_3$ (50 mg, 0.60 mmol) were added to a 50% aqueous dioxane solution (0.3 ml) and mixed, and the mixture was stirred at room temperature for 1 hour. After the reaction was completed, the solvent was distilled off under reduced pressure to remove dioxane, and the solution was washed with ethyl acetate (3 mL×2). The aqueous layer was acidified with 1M HCl, and the solution was extracted with ethyl acetate (3 mL×2) and dried over magnesium sulfate to remove water in the organic layers, and then the solvent was distilled off under reduced pressure. The residue (N-acetyl-Phe-OH) was mixed with triethylamine (24 mg, 1.2 mmol) and chloroacetonitrile (0.1 mL) in dimethylformamide (0.2 ml), and the reaction mixture was stirred at room temperature for 12 hours. After the reaction was completed, diethyl ether (9 ml) was added, and the solution was washed with 1M hydrochloric acid (3 mL×3), saturated $NaHCO_3$ (3 mL×3) and brine (5 mL×1) and dried over magnesium sulfate to remove water in the organic layers, and then the solvent was distilled off under reduced pressure. The crude residue was purified by column chromatography on silica gel to give N-acetyl-Phe-CME (28 mg, 55%).

1.3. Peptide Substrates

All of the peptides were synthesized by solid-phase synthesis using Fmoc chemistry. The N-Fmoc amino acid (N-protected amino acid) used was purchased from Watanabe Chemical Industries, Ltd. (Japan).

As an example of a typical procedure for synthesizing peptide substrates containing CME (peptide-CME), the synthesis of H-$^D$Phe-$^D$Phe-Phe-CME is explained. First, H-$^D$Phe-$^D$Phe-Phe-OH was synthesized by a solid-phase method using WANG-alko-resin (0.15 mmol scale, from Watanabe Chemical Industries, Ltd.). The resulting tripeptide (H-$^D$Phe-$^D$Phe-Phe-OH), Boc$_2$O (35 mg, 0.16 mmol) and NaHCO$_3$ (13 mg, 0.16 mmol) was added to a 50% aqueous dioxane solution (0.5 mL) and mixed, and the mixture was stirred at room temperature for 1 hour. Then, the reaction mixture was distilled off under reduced pressure to remove dioxane, and the solution was washed with ethyl acetate (3 mL×2). The aqueous layer was acidified with 1M HCl, and the solution was extracted with ethyl acetate (3 mL×2) and dried over magnesium sulfate to remove water in the organic layers, and then the solvent was distilled off under reduced pressure. The residue (BOC-$^D$Phe-$^D$Phe-Phe-OH) was mixed with triethylamine (16 mg, 0.16 mmol) and chloroacetonitrile (0.1 mL) in dimethylformamide (0.2 ml), and the reaction mixture was stirred at room temperature for 12 hours. After the reaction was completed, diethyl ether (9 ml) was added, and the solution was washed with 1M hydrochloric acid (3 mL×3), saturated NaHCO$_3$ (3 mL×3) and brine (5 mL×1) and dried over magnesium sulfate to remove water in the organic layers, and then the solvent was distilled off under reduced pressure. The crude residue was dissolved in 4M hydrochloric acid/ethyl acetate (2 ml), and the solution was allowed to stand at room temperature for 20 minutes. Diethyl ether (3 ml) was added and the solvent was distilled off under reduced pressure three times to remove excessive HCl. Diethyl ether (3 ml) was added to form a precipitate, which was recovered by filtration to give a product at a total yield of 43% (35 mg).

2. Synthesis of RNA

All of the oligonucleotides were purchased from Operon Biotechnologies (Japan). tRNA$^{fMet}_{cau}$ was synthesized by in vitro transcription from template DNAs amplified with the following primers.

```
P1:
                                           (SEQ ID NO: 5)
5'-GTAAT ACGAC TCACT ATAGG CGGGG TGGAG CAGCC
TGGTA GCTCG TCGG-3'

P2:
                                           (SEQ ID NO: 6)
5'-GAACC GACGA TCTTC GGGTT ATGAG CCCGA CGAGC TACCA
GGCT-3'

P3:
                                           (SEQ ID NO: 7)
5'-GCATA TGTAA TACGA CTCAC TATAG-3'

P4:
                                           (SEQ ID NO: 8)
5'-TGGTT GCGGG GGCCG GATTT GAACC GACGA TCTTC GGG-3'

P5:
                                           (SEQ ID NO: 9)
5'-TGGTT GCGGG GGCCG GATTT-3'.
```

First, P1 and P2 were annealed and elongated by Taq DNA polymerase. The resulting product was diluted 1:20 in PCR reaction buffer and amplified with P3 and P4 used as 5' and 3' primers, respectively. The product was further diluted 1:200 and amplified with P3 and P5 used as 5' and 3' primers, respectively, to give a DNA corresponding to tRNA$^{fMet}_{cau}$. Then, the DNA product was transcribed with T7 RNA polymerase, and the transcript was purified by 10% denaturing PAGE. The resulting tRNA$^{fMet}_{cau}$ was dissolved in water and the concentration was adjusted to 200 µM.

Similarly, Superflexizymes were also synthesized by in vitro transcription. Specifically, the methods described in Japanese Patent Application No. 2005-352243, entitled "Versatile acylation catalysts and uses thereof", and H. Murakami, A. Ohta, H. Ashigai, H. Suga (2006) "The flexizyme system: a highly flexible tRNA aminoacylation tool for the synthesis of nonnatural peptides" Nature Methods 3, 357-359 were used.

3. Detection of Acylation of tRNA

In the present example, an acylation reaction was performed by using a microhelix or minihelix corresponding to a short analog of the initiator tRNA (tRNA$^{fMet}_{cau}$) instead of the initiator tRNA itself in order to conveniently detect acylation with various amino acids, and the solution after the reaction was analyzed by acrylamide gel electrophoresis under acidic conditions to determine the aminoacylation efficiency. Once a band derived from the minihelix (or microhelix) has been aminoacylated, the mobility decreases. The aminoacylation efficiency can be determined by comparing the intensities of the bands of the minihelix (or microhelix) and the acylated minihelix (or microhelix).

The acylation reaction was performed by reacting 5 µL of 20 µM Superflexizyme (dFx or eFx), 20 µM tRNA analog (microhelix or minihelix), and 5 mM substrate with 20% DMSO in 0.1 M Hepes-K buffer (pH 7.5), 0.1 M KCl, 600 mM MgCl$_2$ at 0° C. for 2 to 6 hours. Specifically, 40 µM tRNA analog was first added to 0.2 M Hepes-K buffer pH 7.5, 0.2 M KCl (2.5 µL), and the mixture was heated at 95° C. for 3 minutes and cooled to 25° C. in 5 minutes. MgCl$_2$ (3 M, 1 µL) and Superflexizyme (200 µM, 0.5 µL) were added, and the mixture was allowed to stand at 25° C. for 5 minutes. An acylation reaction of the tRNA analog was started by adding a substrate (25 mM in DMSO, 1 µL), and the mixture was allowed to stand on ice for 2 hours. The reaction was quenched by adding 15 µL of 0.6 M sodium acetate, pH 5. After ethanol precipitation, the pellet was washed with 70% ethanol and dissolved in 2 µL of 10 mM sodium acetate, Ph 5. After the reaction was completed, the solution was analyzed by 20% denaturing PAGE (50 mM sodium acetate, 6 M urea) under acidic conditions.

The experimental results shown in the attached drawings represent examples in which Phe derivatives having an N-acyl group (FIGS. 6 to 7) and others were used as substrates. The results of acylation are shown in FIGS. 8 to 11. Here, it was found that a wide variety of amino acid derivatives were efficiently acylated by Superflexizymes.

The abbreviations for the substrates shown as examples have the following meanings. F=phenylalanine (Phe), OH-F=hydroxy-deamino-phenylalanine, Ac=acetyl, N3Ac=azido-acetyl, oxP=4-oxo-pentanoyl, Pen=pent-4-enoyl, Hex=hexanoyl, Pyl=pent-5-enoyl, CBA=carboxybenzylamine, Mhe=5-methyl-hexanoyl, Mim=maleimide, PyE=pyroglutamine, $^D$Phe=D-phenylalanine.

4. Translation

In the present example, polypeptides having a desired N-terminal structure were translationally synthesized by adding an initiator tRNA acylated with various amino acids to a cell-free translation system to initiate a translation.

The translation system used was PURESYSTEM® from PGI, which is a prokaryotic-derived reconstructed cell-free protein synthesis system including a transcription system from cDNA. Acylated tRNAs were added to translation reaction mixtures containing only minimum necessary amino acids. At the same time, $C^{14}$-labeled Asp was added for the detection of peptides produced. After the translation reaction, the product was analyzed by tricine-SDS PAGE.

First, an acylated initiator tRNA for use in the translation reaction was prepared. In 0.1 M Hepes-K buffer pH 7.5, 0.1 M KCl, 600 mM $MgCl_2$, 15 μL of 20 μM Superflexizyme (dFx or eFx), 20 μM $tRNA^{fMet}{}_{CAU}$, and 5 mM substrate were reacted with 20% DMSO at 0° C. for 2 to 6 hours, and then the mixture was precipitated with ethanol to isolate an initiator tRNA acylated with an amino acid of interest ($tRNA^{fMet}{}_{cau}$ or a variant having a different anticodon). Specifically, 40 μM $tRNA^{Asn}{}_{CUA}$ (or a variant thereof) was added to 0.2 M Hepes-K buffer pH 7.5, 0.2 M KCl (7.5 μL), and the mixture was heated at 95° C. for 3 minutes and cooled to 25° C. in 5 minutes. $MgCl_2$ (3 M, 3 μL) and Superflexizyme (200 μM, 1.5 μL) were added, and the mixture was allowed to stand at 25° C. for 5 minutes. An acylation reaction was started by adding a substrate (25 mM in DMSO, 3 μL), and the mixture was allowed to stand on ice for 2 hours. After the acylation reaction, the reaction was quenched by adding 45 μL of 0.6 M sodium acetate (pH 5), and RNA was recovered by ethanol precipitation. The pellet was washed twice with 70% ethanol and 0.1 M sodium acetate (pH 5), and once with 70% ethanol to give an acylated initiator tRNA. The acylated initiator tRNA was dissolved in 0.5 μL of 1 mM sodium acetate immediately before it was added to a translation mixture.

Ribosomal synthesis of peptides was performed by adding 0.04 μM cDNA and 3 mM EDTA, 200 μM Thr, Tyr, Lys or Thr, Gly, Phe, Tyr, Lys as minimum necessary amino acids for elongation reaction and 50 μM [$^{14}$C]-Asp, and 120 μM acylated $tRNA^{fMet}{}_{CAU}$ to a translation reaction mixture using a PURE system. After translation reaction at 37° C. for 1 hour, the product was analyzed by tricine-SDS PAGE.

Figure 16:
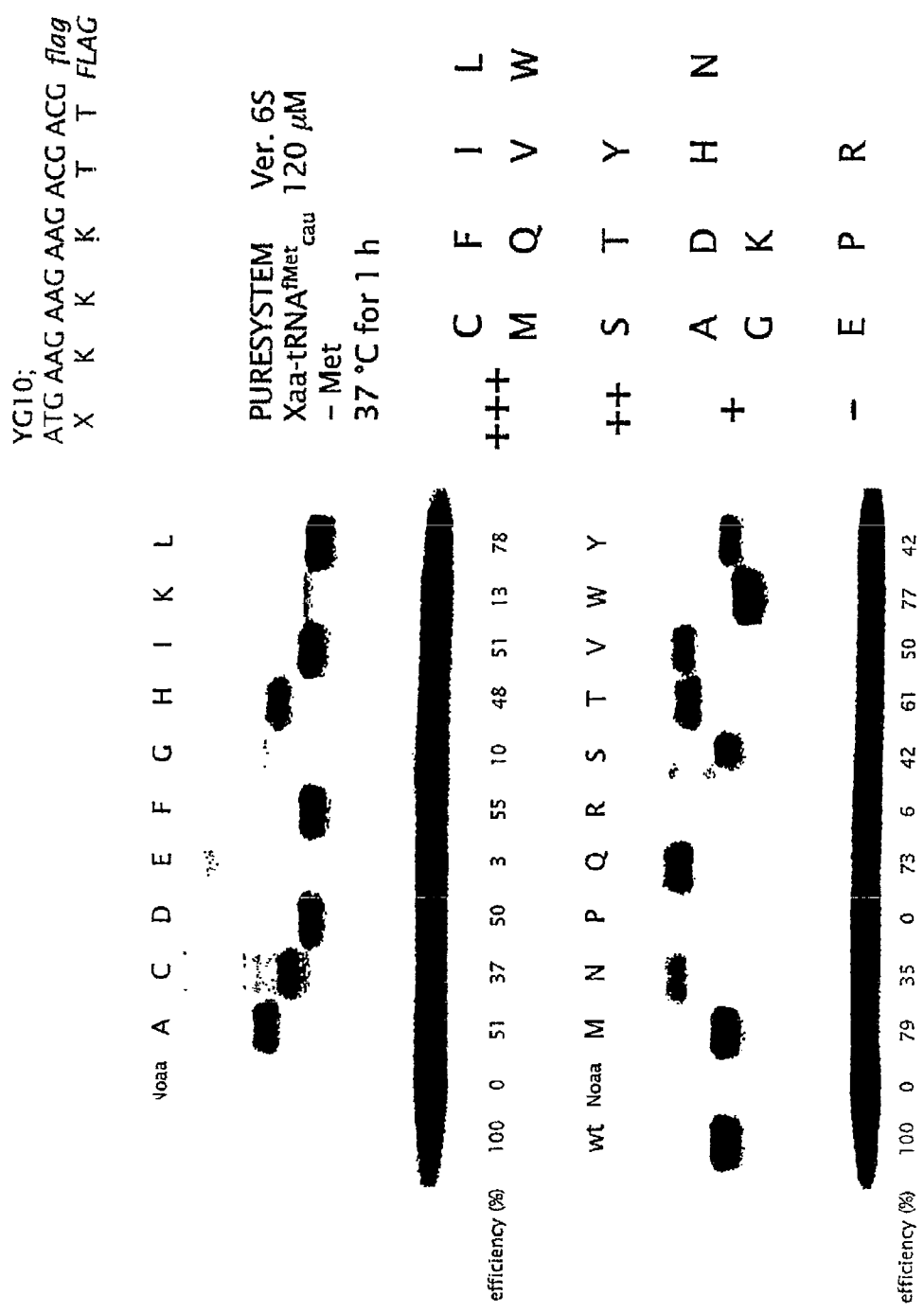
FIG. 16 (YG10—SEQ ID NO: 12 (DNA) and SEQ ID NO: 13 (peptide)) shows examples in which translational polypeptide synthesis was initiated with the twenty natural amino acids.
Figure 17:
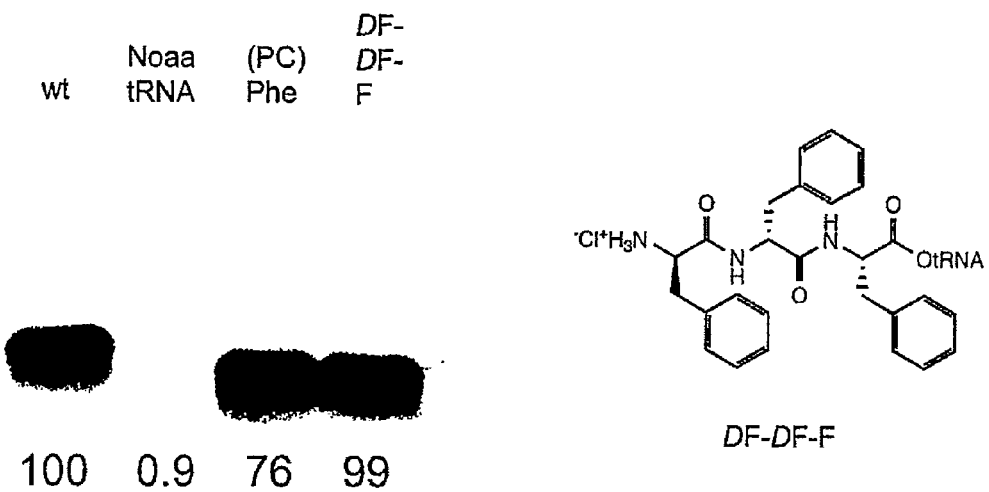
FIG. 17 shows an example in which translation was initiated with a tripeptide containing two D-amino acids.
Figure 18:
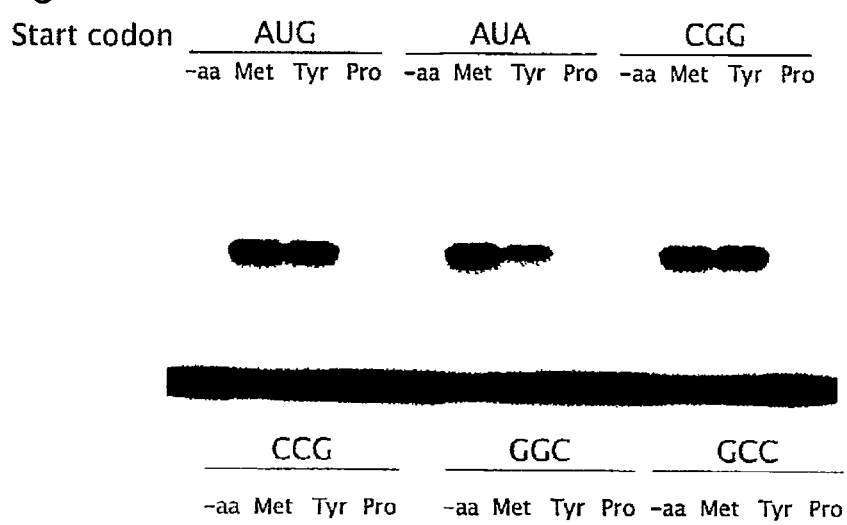
FIG. 18 shows that translation can also be initiated with four codons other than the common start codon.
Figure 19:
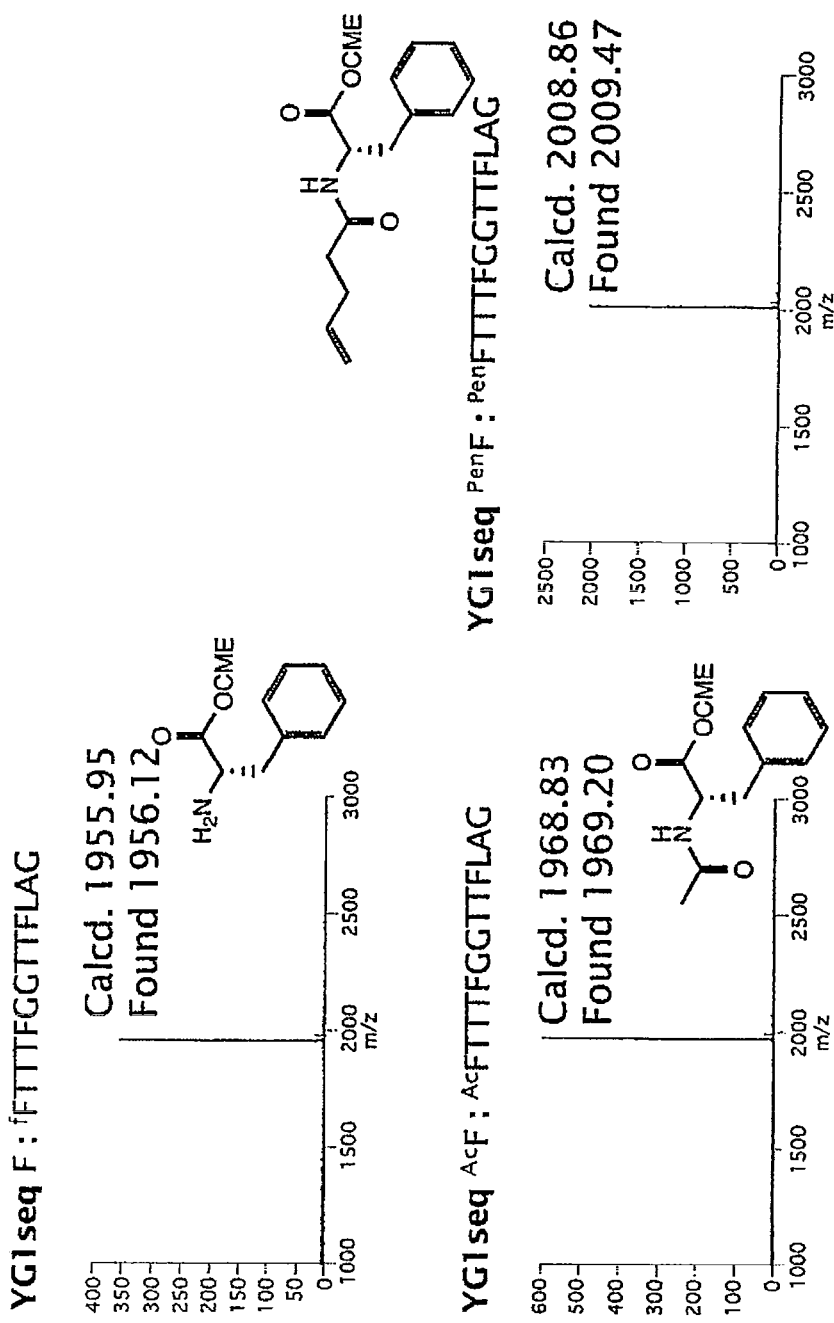
FIG. 19 (SEQ ID NOS: 18, 19, and 20) shows mass spectra of peptide translation products synthesized in FIGS. 12 to 15.
Figure 20:
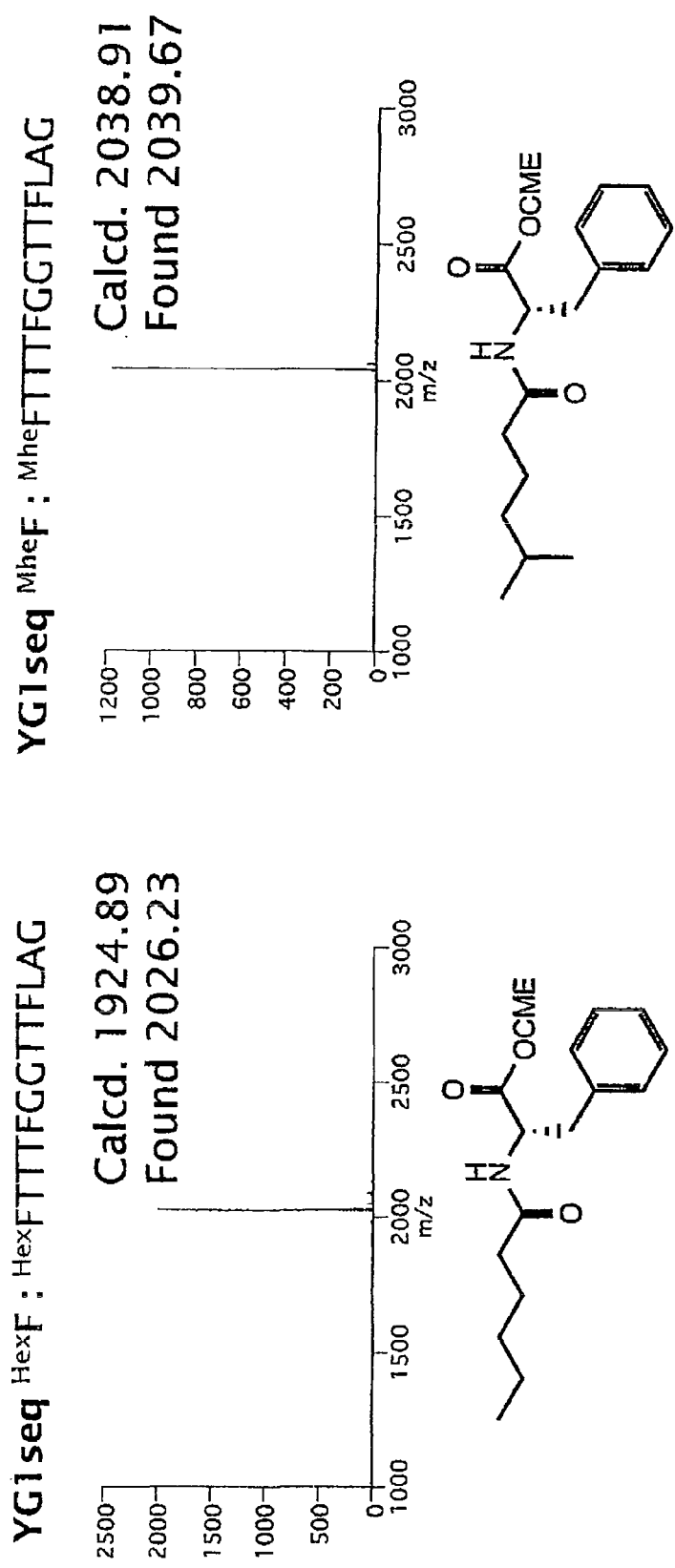
FIG. 20 (SEQ ID NOS: 21 and 22) shows mass spectra of peptide translation products synthesized in FIGS. 12 to 15.
Figure 21:
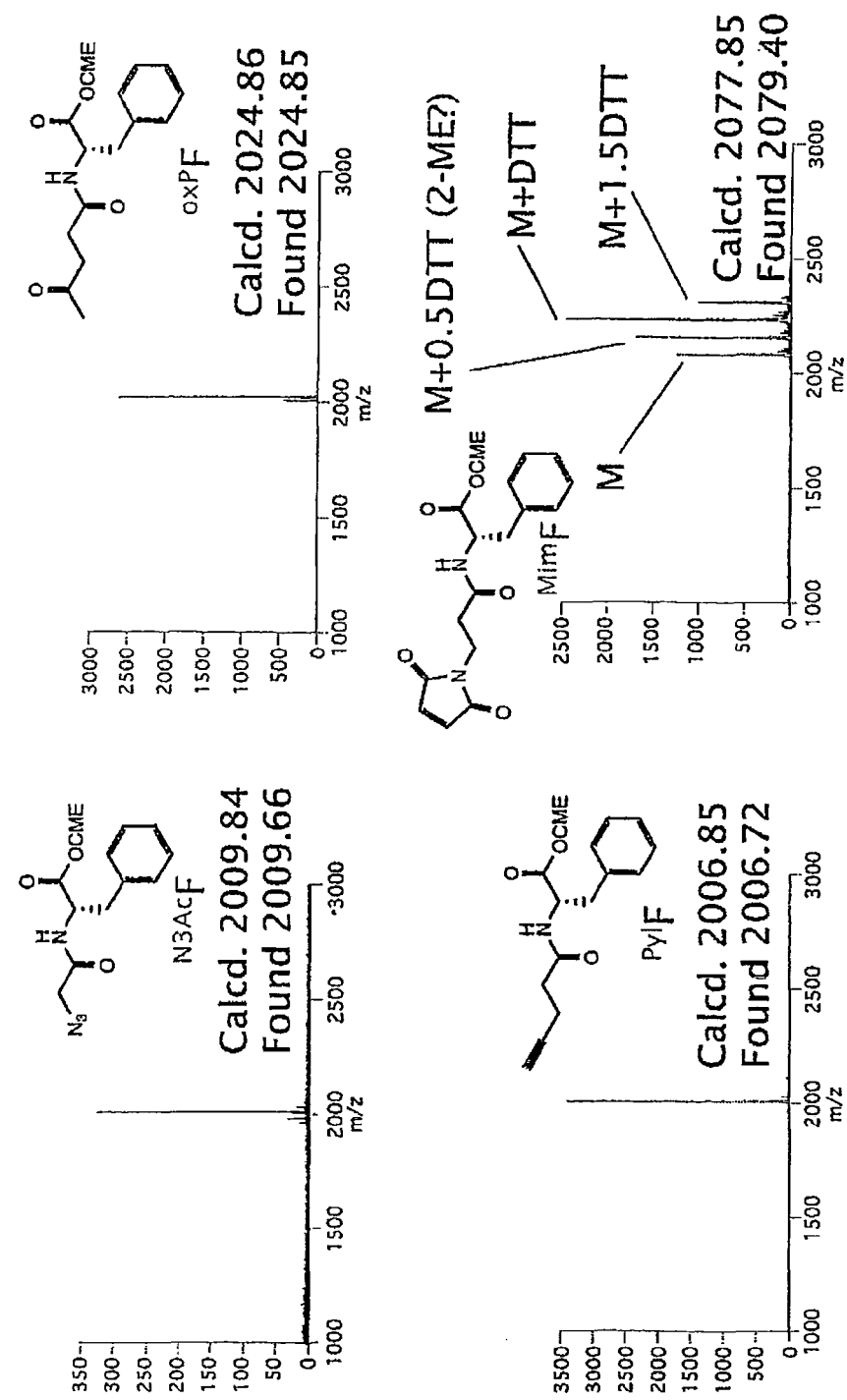
FIG. 21 shows mass spectra of peptide translation products synthesized in FIGS. 12 to 15.

The results are shown in FIGS. 12 to 18. All the figures except for FIG. 18 show examples in which a methionine codon (ATG) was as an N-terminal start codon and $tRNA^{Asn}{}_{CUA}$ was used as an initiator tRNA (from the template cDNA sequence shown as YG1 or YG10 in the figures), but other cDNA sequences also seemed to be usable for translational synthesis reaction without any limitation. In addition, unnatural amino acids can also be introduced into the middle of the peptide sequence of YG1 by reading F in the middle of the peptide sequence by a suppressor tRNA (T and G surrounding F are spacers), though such a case is not shown in the present example. An FLAG sequence is present at the C-terminus of the peptide as a purification tag.

Figure 6:
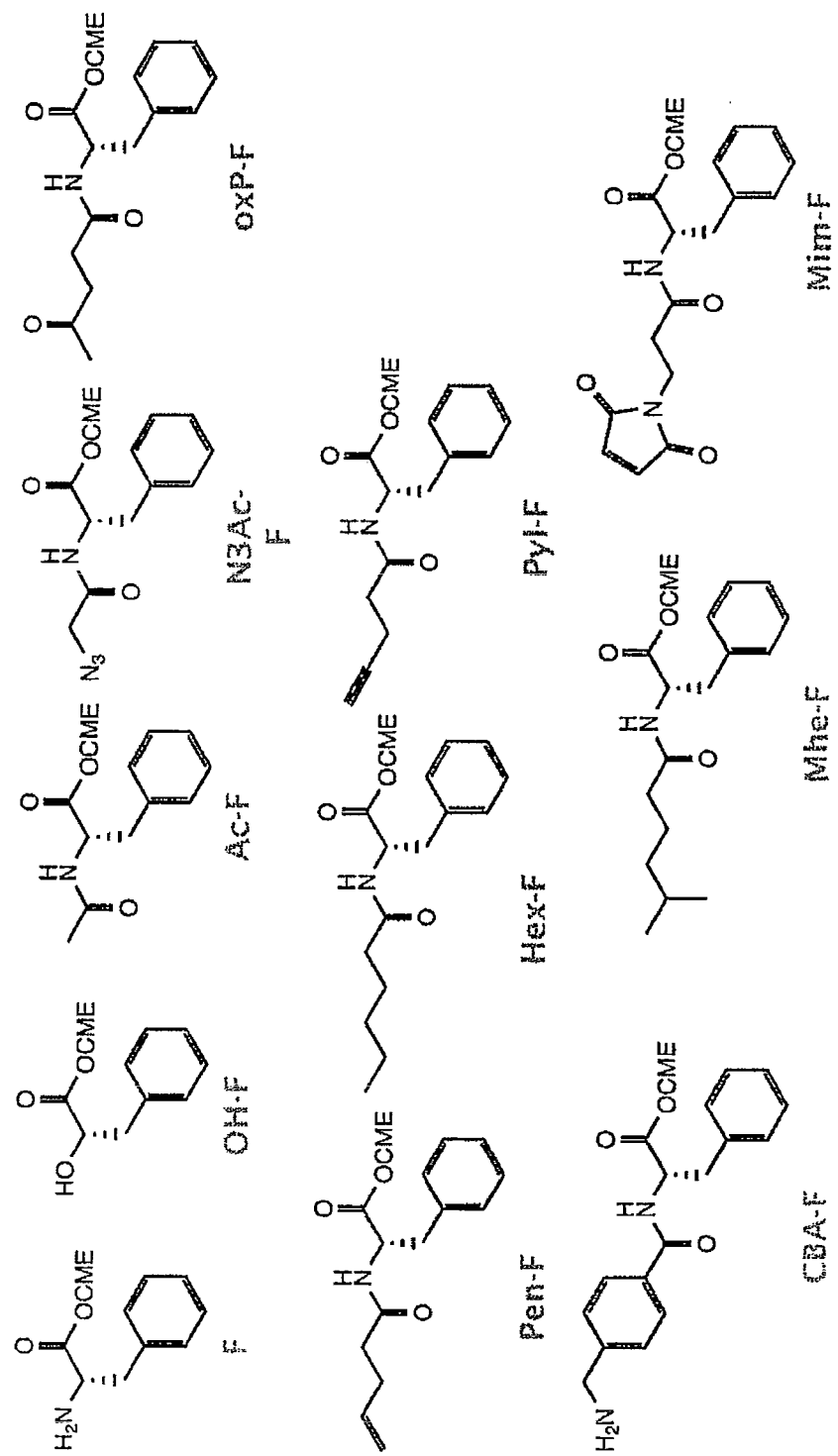
FIG. 6 shows amino acid derivatives (N-acyl Phe derivatives) used in the examples.
Figure 7:
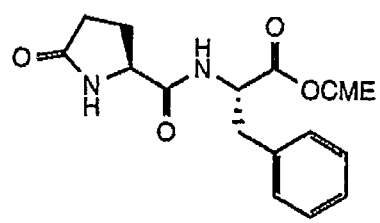
FIG. 7 shows amino acid derivatives used in the examples. Two examples of dipeptide derivatives are shown in the upper line, and two examples of D-phenylalanine derivatives are shown in the lower line.
Figure 7:
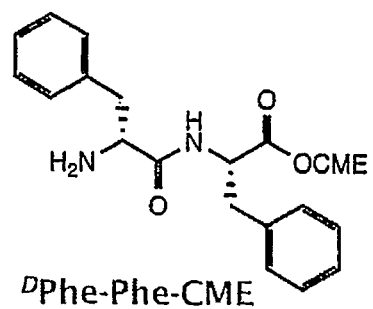
Figure 7:
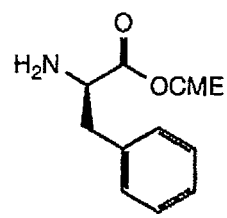
Figure 7:
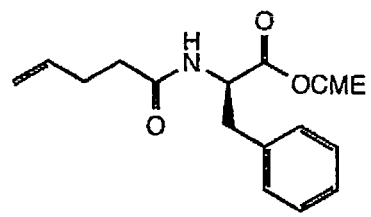
Figure 8:
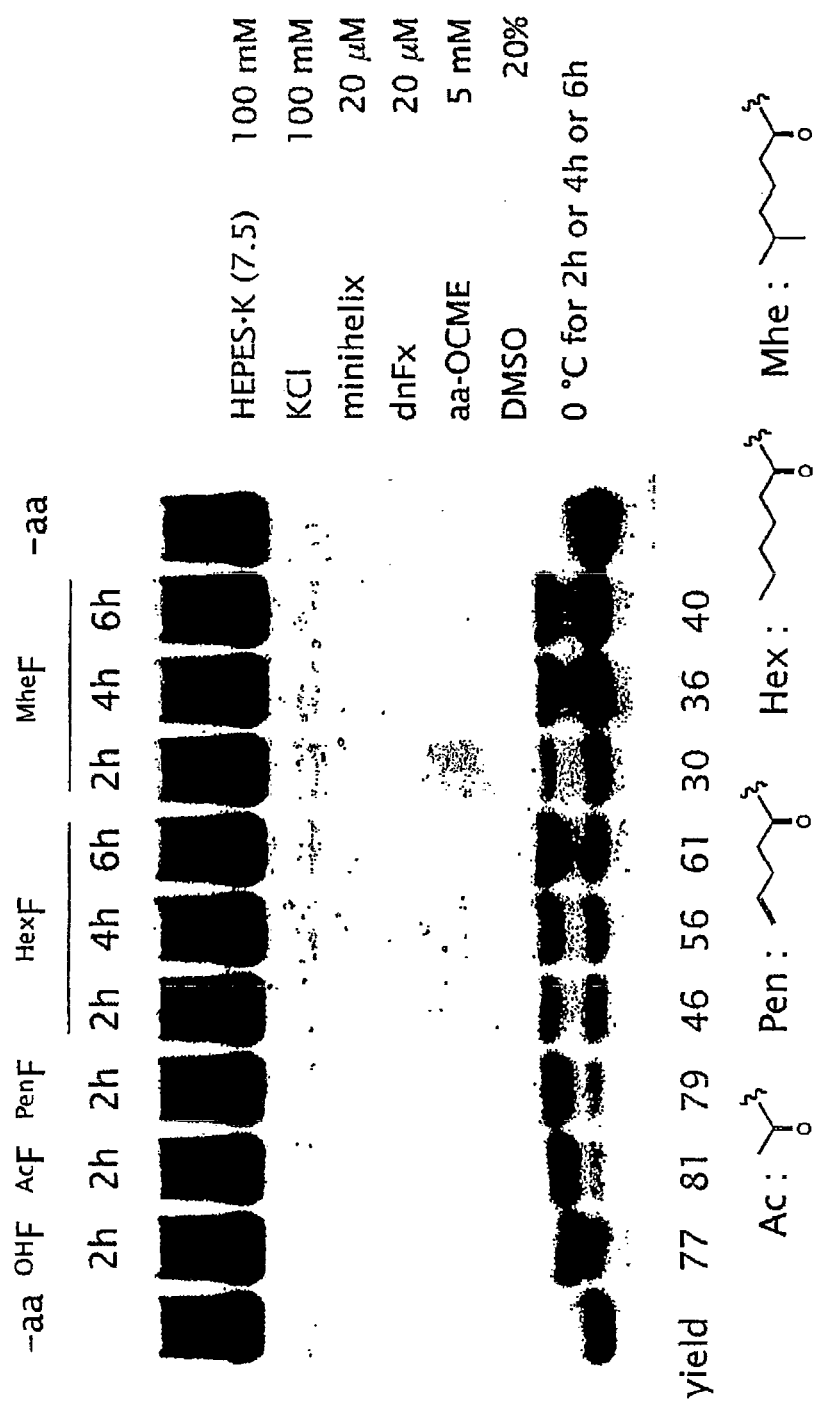
FIG. 8 shows the observed results of the acylation efficiencies of the amino acid derivatives listed in FIG. 6 and FIG. 7. The values below the lanes represent the yields (2 hours or 4 hours or 6 hours at 0° C.).
Figure 9:
FIG. 9 shows the observed results of the acylation efficiencies of the amino acid derivatives listed in FIG. 6 and FIG. 7.
Figure 10:
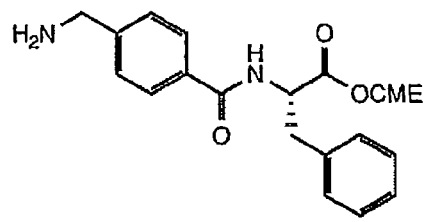
FIG. 10 shows the observed results of the acylation efficiencies of the amino acid derivatives listed in FIG. 6 and FIG. 7.
Figure 11:
FIG. 11 shows the observed results of the acylation efficiencies of the amino acid derivatives listed in FIG. 6 and FIG. 7.

FIGS. 12 to 15 show experiments made to examine whether or not a peptide is translated using the initiator tRNA charged with the amino acid derivatives listed in FIGS. 6 to 7.

Figure 12:
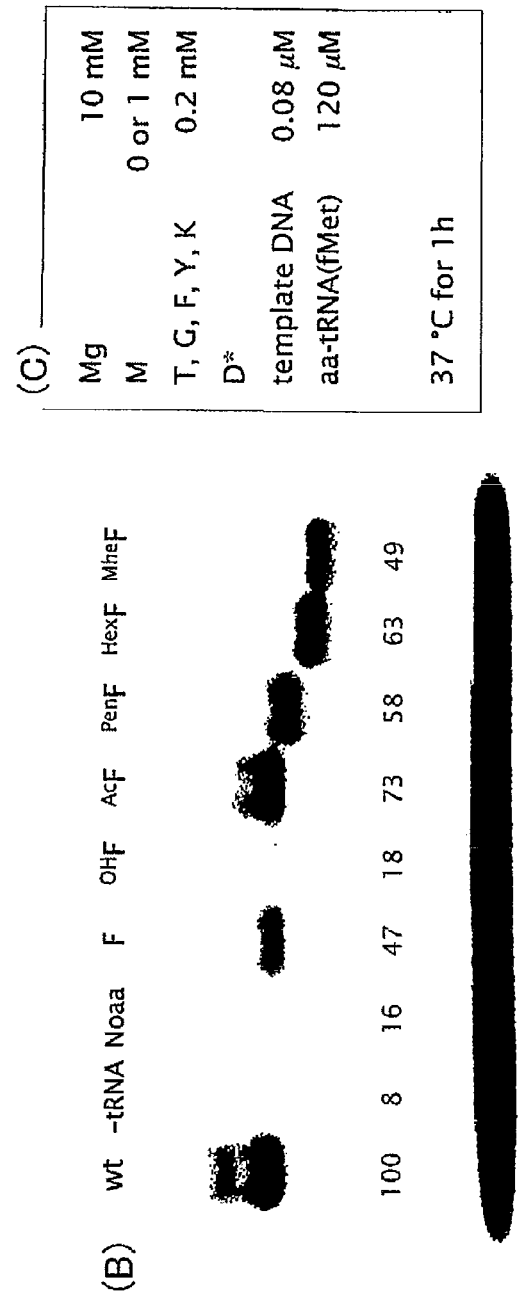
FIG. 12 shows examples in which translational polypeptide synthesis was initiated with various amino acids.

In FIG. 12, peptide synthesis was initiated with phenylalanine having various fatty acid-like acyl groups. Here, YG1 was used as the cDNA sequence, and Thr, Gly, Phe, Tyr, Lys were added as minimum necessary amino acids.

[Formula 3]
(SEQ ID NOS: 10 and 11)
YG1; ATG ACG ACG ACG TTC GGG GGG ACG ACG flag
      M   T   T   T   F   G   G   T   T   FLAG In the positive control containing methionine in the system (wt), bands certainly appeared, showing that peptide synthesis occurred. In the negative controls containing no initiator tRNA (−tRNA) or containing an unacylated initiator tRNA (Noaa) in the absence of methionine, however, no band appeared, showing that peptide synthesis was inhibited. When the initiator tRNA acylated with phenylalanine having various fatty acid-like acyl groups was added, peptide synthesis was observed, suggesting that the translation reaction was initiated with these phenylalanine derivatives.

Figure 13:
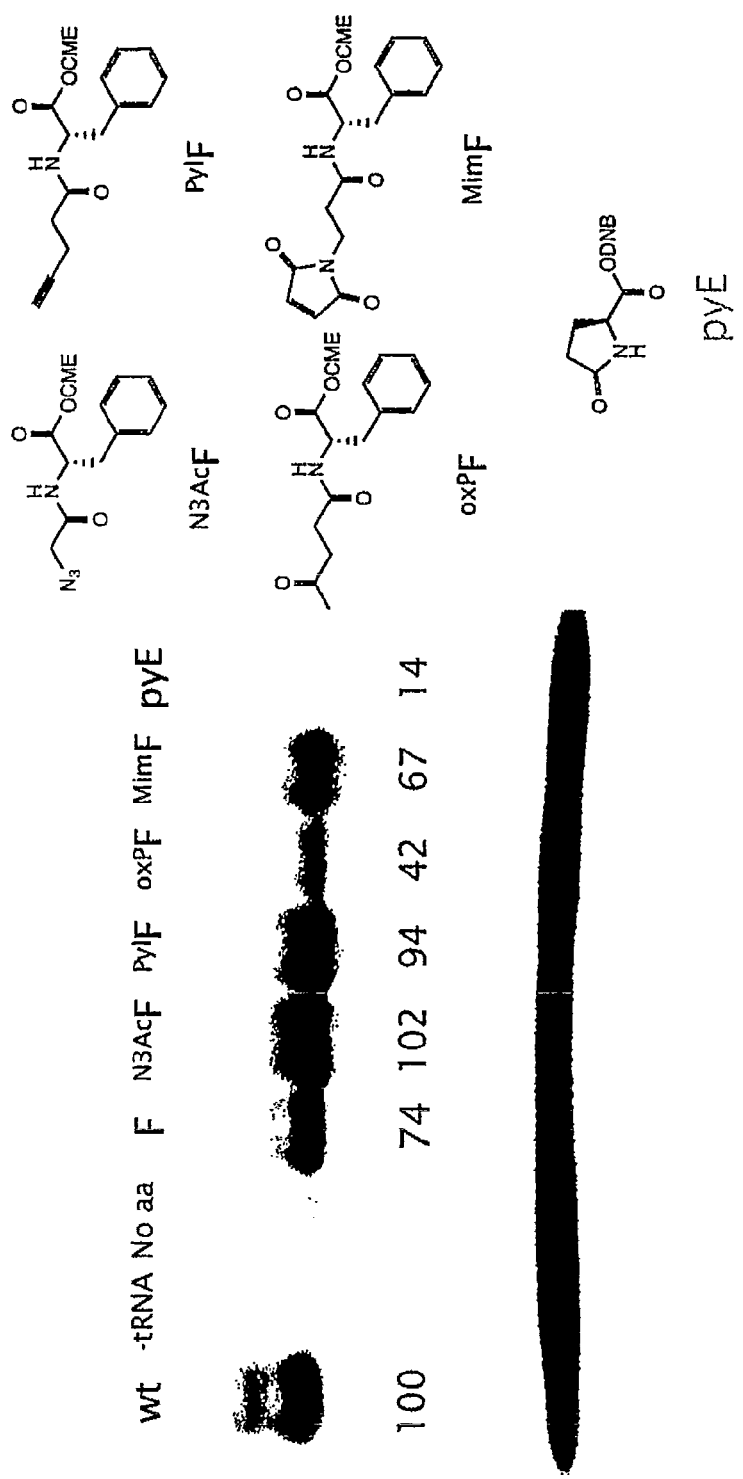
FIG. 13 shows examples in which translational polypeptide synthesis was initiated with various amino acids.

In FIG. 13, translation was initiated with phenylalanine having various acyl groups by using YG1 as cDNA in the same manner as in FIG. 12. Here, acyl groups having functional groups susceptible to post-translational chemical modification ($^{N3Ac}F$ (azido group), $^{Pyl}F$ (alkyne), $^{oxP}F$ (keto group), $^{Mim}F$ (maleimide group)) were used.

Figure 14:
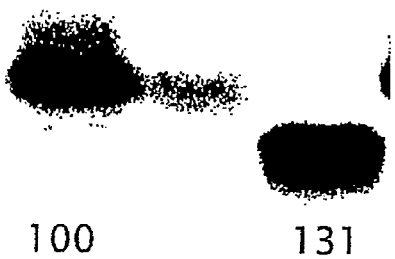
FIG. 14 shows examples in which translational polypeptide synthesis was initiated with various amino acids.
Figure 14:
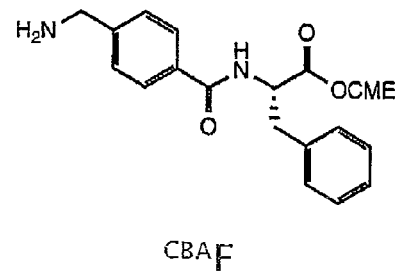

In FIG. 14, translation was initiated with phenylalanine acylated with carboxy-benzylamine ($^{CBA}F$) also using YG1 as cDNA. Translation reaction was successfully initiated even with such a sterically bulky acyl group.

Figure 15:
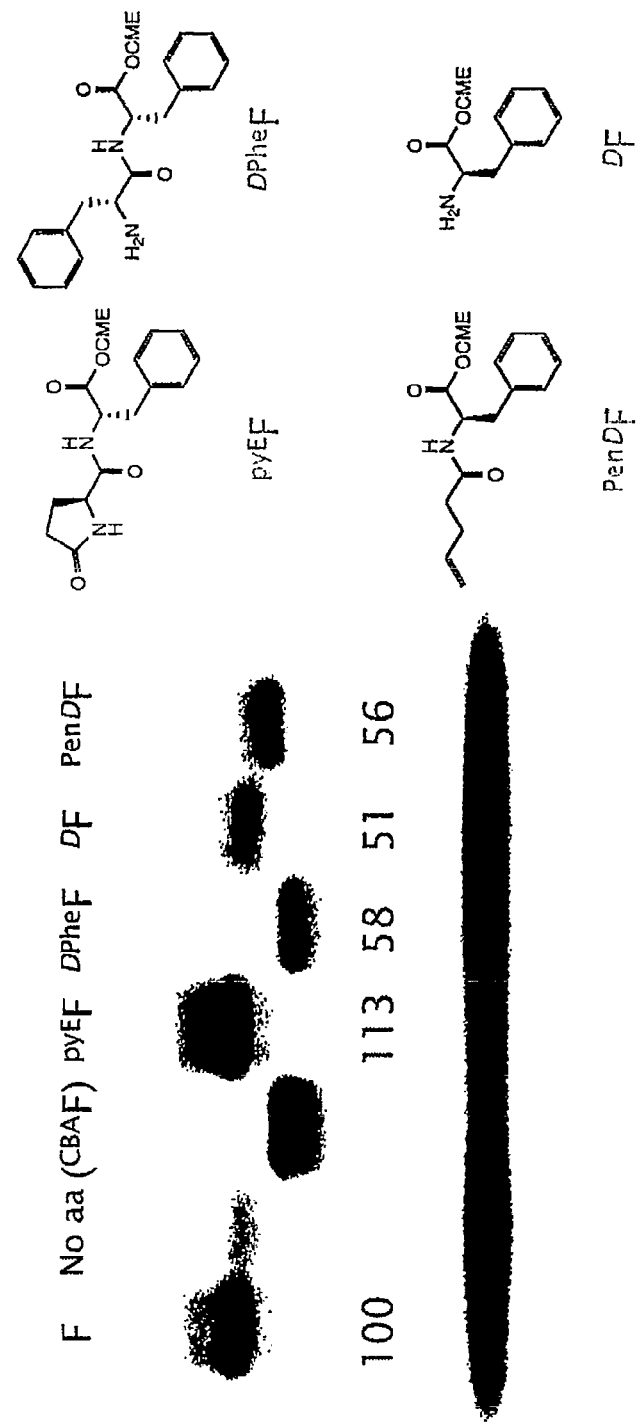
FIG. 15 shows examples in which translational polypeptide synthesis was initiated with various amino acids.

In FIG. 15, translation was initiated with various phenylalanine derivatives also using YG1 as cDNA. Here, phenylalanine acylated with pyroglutamic acid ($^{pyE}F$) frequently found at the N-termini of peptide hormones and D-phenylalanine ($^{DPhe}F$) as a D-amino acid was used. It was shown that translation can also be initiated with D-phenylalanine ($^DF$) or N-acylated D-phenylalanine ($^{PenD}F$) though L-phenylalanine has been conventionally used.

FIG. 16 shows examples in which the initiator tRNA aminoacylated with each of the twenty natural amino acids was used for the translational synthesis of polypeptides. As a result, translation was successfully initiated with the all amino acids except for a few ones (Pro, Glu, Arg). (Here, YG10 was used as cDNA.)

[Formula 4]
(SEQ ID NO: 12 and 13)
YG10; ATG AAG AAG AAG ACG ACG flag
       X   K   K   K   T   T   FLAG FIG. 17 shows that translation can also be initiated with the initiator tRNA acylated with a tripeptide (initiator peptidyl-tRNA). (Here, YG10 was used as cDNA.) It should be noted that two D-amino acids are contained.

FIG. 18 shows that translation can also be initiated with four codons other than the common start codon. Translation initiation reaction was performed using a cDNA sequence containing an initiator tRNA in which the anticodon region in the native initiator tRNA was changed from AUG to AUA, CGG, CCG, GGC, and GCC and a cognate start codon. In the experiment, the tRNA charged with no amino acid (−aa, negative control) and the tRNA charged with each of Met, Tyr and Pro were used. Pro is one of amino acids with which translation cannot be initiated for unknown reasons among the twenty natural amino acids shown in FIG. 16 and still failed to initiate a translation even if the start codon was changed, but translation was successfully initiated with the other amino acids without difficulty. This experiment showed that sequences other than the native start codon (AUG) can also be assigned as start codons.

Thus, it was found that polypeptides containing at the N-termini a wide variety of N-acylamino acids, D-amino acids and polypeptide structures including unique structures can be translationally synthesized and that the start codon can be modified.

5. Mass Spectrometry of Peptides

The molecular masses of peptide translation products were determined by mass spectrometry. Peptides were translationally synthesized using Asp in place of [$^{14}$C]-Asp by the method described above, and then the products were isolated from the translation mixtures by using a FLAG tag sequence attached to the C-termini of the products. ANTI-FLAG® M2 agarose commercially available from SIGMA was used for the isolation. The isolates were analyzed by MALDI-MS to verify that the molecular masses of the products agreed with estimated molecular masses and that any undesired impurities (such as peptides containing N-terminal formylmethionine) were not included.

The results are shown in FIGS. 19 to 25. FIGS. 19 to 24 show mass spectra of polypeptides having various N-terminal structures synthesized in FIGS. 12 to 15, and FIG. 25 shows a mass spectrum of the translation product initiated with the tripeptide shown in FIG. 17 (as shown below).

[Formula 5]

```
(SEQ ID NO: 15 and 16)
YG1; ATG ACG ACG ACG TTC GGG GGG ACG ACG flag
  DF-DF-F  T    T    T    F   G   G   T    T   FLAG
```

The estimated molecular masses and observed molecular masses of the polypeptides agreed with each other and only single peaks of the targets were observed in the mass spectra, showing that only the target polypeptides were synthesized and that any peptide or the like derived from the native translation initiation machinery was not included.

Figure 22:
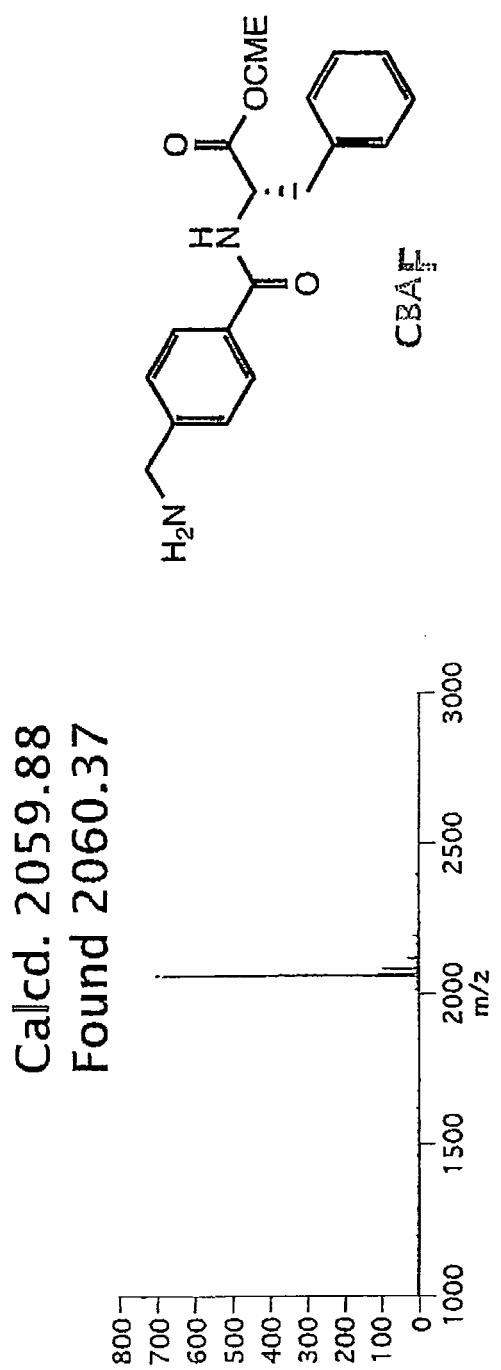
FIG. 22 shows a mass spectrum of a peptide translation product synthesized in FIGS. 12 to 15.
Figure 23:
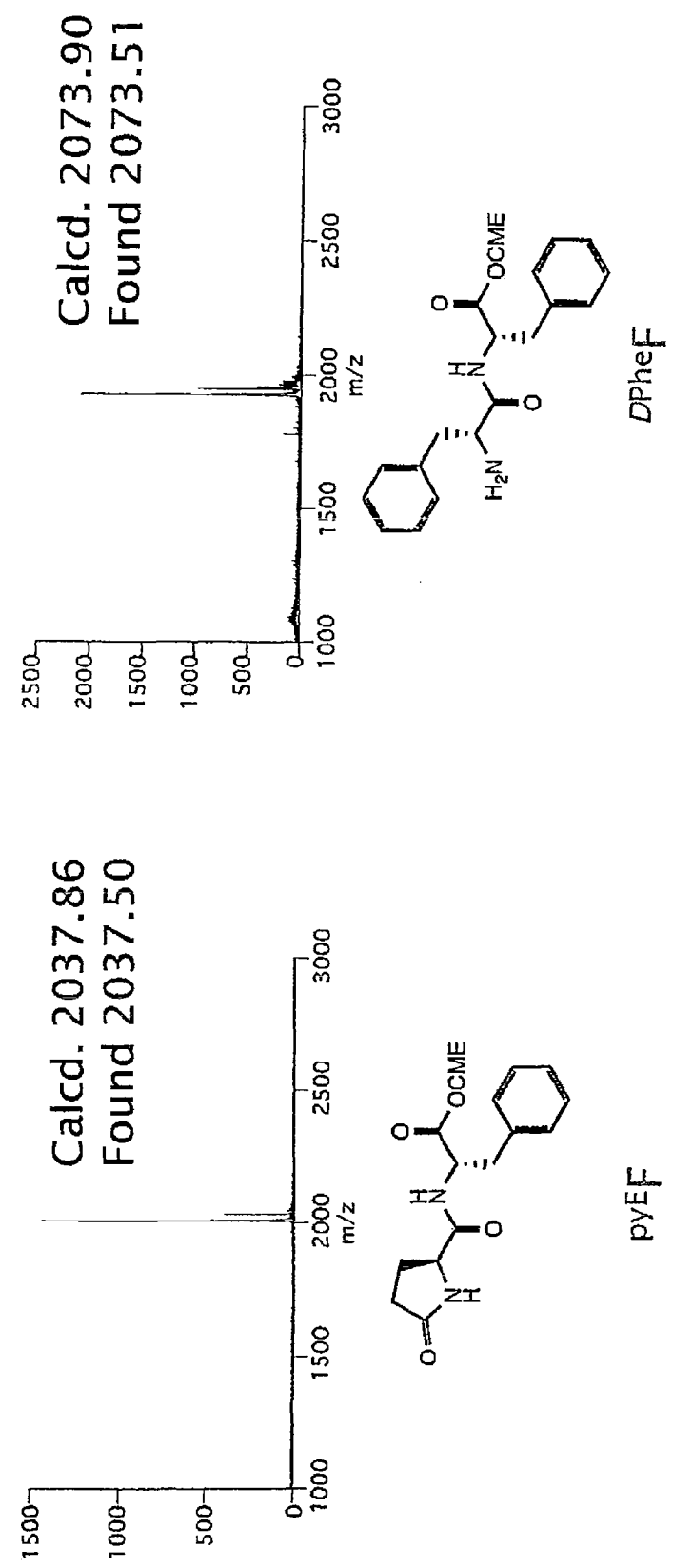
FIG. 23 shows mass spectra of peptide translation products synthesized in FIGS. 12 to 15.
Figure 24:
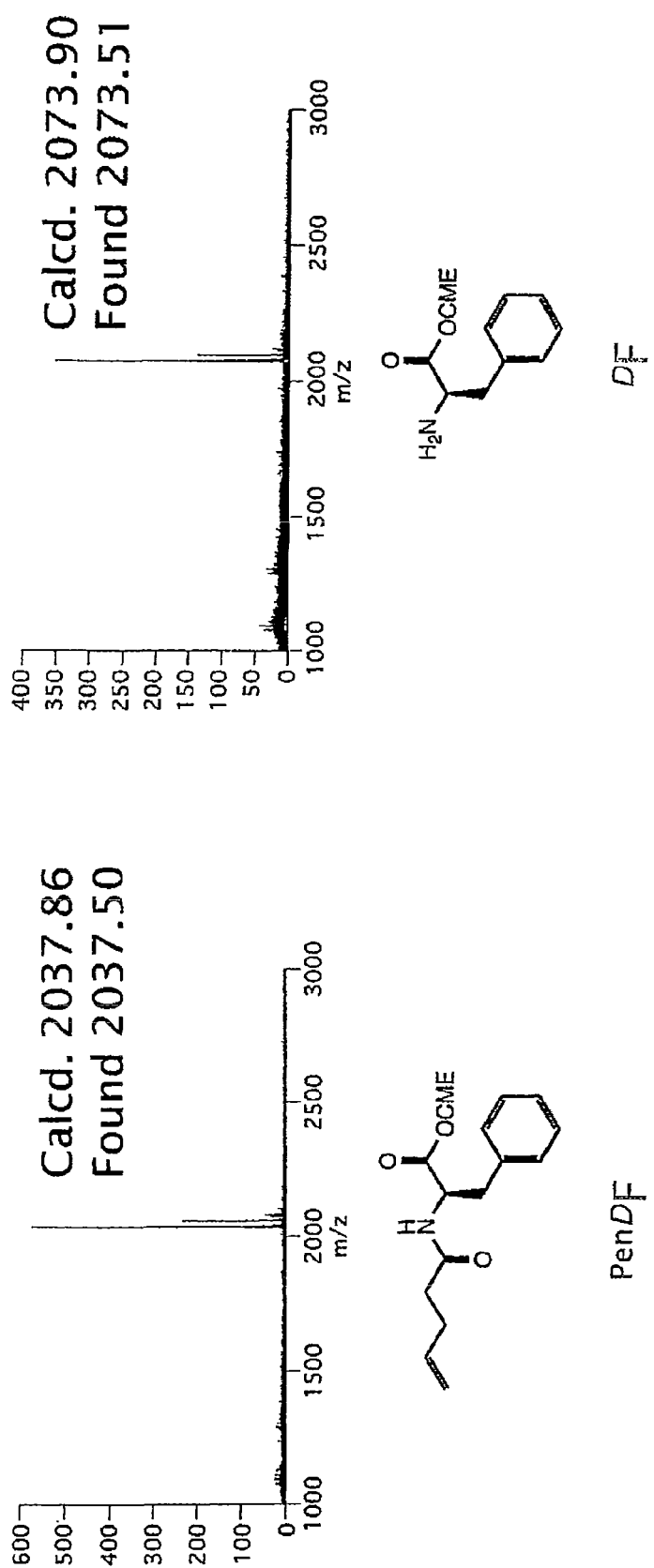
FIG. 24 shows mass spectra of peptide translation products synthesized in FIGS. 12 to 15.
Figure 25:
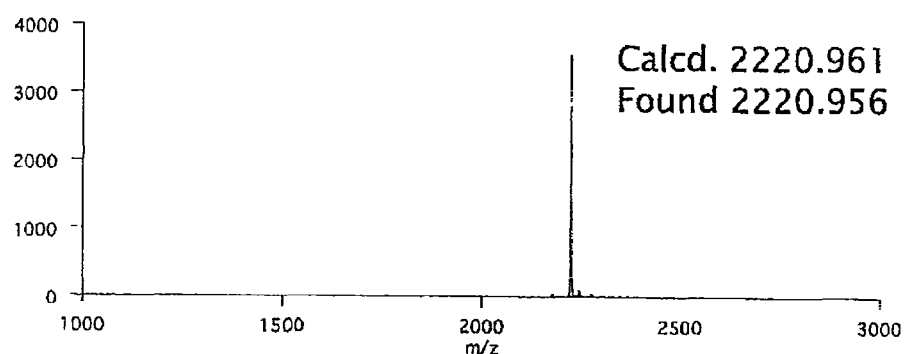
FIG. 25 (SEQ ID NO: 15 (DNA)) shows a mass spectrum of the peptide translation product initiated with the tRNA acylated with the tripeptide (DF-DF-F) shown in FIG. 17.

In addition, new findings were obtained about formylation of N-terminal amino groups. FIG. 22 shows that the N-terminus of the translation product initiated with $^{CBA}F$ (a derivative of phenylalanine acylated with benzylamine) (FIG. 14) was not formylated even in the presence of MTF. FIG. 23 shows that no formylation occurred when a dipeptide attached to the initiator tRNA was used for translation. FIG. 24 shows that a polypeptide having a D-amino acid at the N-terminus was also translationally synthesized without any difficulty and that the N-terminus of D-phenylalanine ($^{D}F$) was not formylated. On the other hand, formylation has been observed when translation was initiated with L-phenylalanine.

The invention claimed is:

1. A process for translationally synthesizing a polypeptide having a desired N-terminal structure, comprising the steps of:
   (a) providing a ribozyme capable of catalyzing the acylation reaction of tRNA;
   (b) providing an amino acid substrate having a desired structure for use as a substrate for the acylation reaction by the ribozyme;
   (c) performing an acylation reaction of an initiator tRNA with the amino acid substrate in (b) above using the ribozyme in (a) above to give an initiator tRNA aminoacylated with the amino acid having a desired structure;
   (d) adding the aminoacylated initiator tRNA obtained in (c) above to a cell-free translation system lacking methionine or methionyl-tRNA synthetase (MetRS) to initiate a translation with the amino acid having a desired structure, thereby giving a polypeptide having a desired N-terminal structure,
   wherein said amino acid that aminoacylates the initator tRNA in step (c) is a common amino acid other than methionine and is selected from the group consisting of alanine (Ala), valine (Val), leucine (Leu), isoleucine (Ile), proline (Pro), tryptophan (Trp), phenylalanine (Phe), glycine (Gly), serine (Ser), threonine (Thr), tyrosine (Tyr), cysteine (Cys), glutamine (Gln), asparagine (Asn), lysine (Lys), arginine (Arg), histidine (His), aspartate (Asp), and glutamate (Glu), or said amino acid is an unusual amino acid.

2. The process of claim 1 wherein the unusual amino acid is selected from the group consisting of amino acids containing various acyl groups in their amino groups, D-amino acids, beta-amino acids, gamma-amino acids, delta-amino acids, and N-methylated derivatives of these amino acids, pyroglutamic acids, statins (beta-hydroxy-gamma-amino acids) and derivatives thereof, dipeptides, tripeptides and longer peptides.

3. The process of claim 1 wherein the amino acid substrate provided in step (b) is an amino acid derivative having a modestly activated ester bond.

4. The process of claim 1 wherein the amino acid substrate is a cyanomethyl ester, dinitrobenzyl ester or 4-chlorobenzyl thioester of an amino acid.

5. The process of claim 1 wherein the ribozyme capable of catalyzing the acylation reaction of tRNA is a ribozyme consisting of the RNA sequence (1) or (2) below;

(1)
(SEQ ID NO: 3)
GGAUCGAAAGAUUUCCGCGGCCCCGAAAGGGGAUUAGCGUUAGGU (2)
(SEQ ID NO: 4)
GGAUCGAAAGAUUUCCGCAUCCCCGAAAGGGUACAUGGCGUUAGGU.

6. The process of claim 1 wherein the initiator tRNA has a structure consisting of the RNA sequence in the 5'-3' direction shown by:

(SEQ ID NO: 2)
GGCGGGGUGGAGCAGCCUGGUAGCUCGUCGGGCU<u>NNN</u>AACCCGAAGAUC

GUCGGUUCAAAUCCGGCCCCCGCAACCA where NNN represents an anticodon consisting of a random nucleotide set, and a start codon corresponding to the anticodon exists on the mRNA encoding the sequence of the polypeptide to be transiationally synthesized, and the start codon encodes the amino acid having a desired structure.

7. The process of claim 6 wherein the anticodon in the initiator tRNA is CAU and the start codon on the mRNA is AUG.

8. The process of claim 6 wherein the anticodon in the initiator tRNA is an anticodon other than CAU and the start codon on the mRNA is a codon other than AUG.

9. The process of claim 1, which uses a reconstructed cell-free translation system as the cell-free translation system and the process further controls N-terminal formylation of the polypeptide to be translationally synthesized by selecting the presence or absence of a methionine tRNA formyltransferase (MTF).

10. The process of claim 1 wherein the amino acid that aminoacylates the initiator tRNA in step (c) is an unusual amino acid.

11. A process for translationally synthesizing a polypeptide having a desired N-terminal structure, comprising the steps of:
   (a) providing as ribozyme capable of catalyzing the acylation reaction of tRNA;
   (b) providing an amino acid substrate having a desired structure for use as a substrate for the acylation reaction by the ribozyme;
   (c) performing an acylation reaction of an initiator tRNA that has an anticodon other than CAU with the amino acid substrate in (b) above using the ribozyine in (a) above to give an initiator tRNA that has an anticodon other than CAU aminoacylated with the amino acid having a desired structure;
   (d) adding the aminoacylated initiator tRNA obtained in (c) above to a cell-free translation system to initiate a translation with the amino acid having a desired structure, thereby giving a polypeptide having a desired N-terminal structure, wherein said amino acid that aminoacylates the initiator tRNA in step (c) is a common amino acid other than methionine and is selected from the group consisting of alanine (Ala), valine (Val), leucine (Leu), isoleucine (Ile), proline (Pro), tryptophan (Trp), phenylalanine (Phe), glycine (Gly), serine (Ser), threonine (Thr), tyrosine (Tyr), cysteine (Cys), glutamine (Gln), asparagine (Asn), lysine (Lys), arginine (Arg), histidine (His), aspartate (Asp), and glutamate (Glu), or said amino acid is an unusual amino acid.

12. The process of claim 11 wherein the unusual amino acid is selected from the group consisting of amino acids containing various acyl groups in their amino groups, D-amino acids, beta-amino acids, gamma-amino acids, delta-amino acids, and N-methylated derivatives of these amino acids, pyroglutamic acids, statins (beta-hydroxy-gamma-amino acids) and derivatives thereof, dipeptides, tripeptides and longer peptides.

13. The process of claim 11, wherein the anticodon corresponds to a start codon selected from the group consisting of AUA, CGG, CCG, GGC and GCC.

14. The process of claim 12, wherein the anticodon corresponds to a start codon selected from the group consisting of AUA, CGG, CCG, GGC and GCC.

15. The process of claim 1, which uses a reconstructed cell-free translation system as the cell-free translation system.

16. The process of claim 11, which uses a reconstructed cell-free translation system as the cell-free translation system.

17. The process of claim 12, which uses a reconstructed cell-free translation system as the cell-free translation system.

* * * * *